United States Patent
Guerrero-Preston et al.

(10) Patent No.: US 10,428,391 B2
(45) Date of Patent: Oct. 1, 2019

(54) METHOD TO USE VIRAL AND HOST METHYLATION MARKERS FOR CERVICAL CANCER SCREENING AND TRIAGE IN LIQUID PREP, SERUM/PLASMA, AND URINE: PCR AND SEQUENCING BASED PROCESS METHODS

(71) Applicant: THE JOHNS HOPKINS UNIVERSITY, Baltimore, MD (US)

(72) Inventors: Rafael Guerrero-Preston, Baltimore, MD (US); David Sidransky, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 52 days.

(21) Appl. No.: 15/747,889

(22) PCT Filed: Jul. 27, 2016

(86) PCT No.: PCT/US2016/044225
§ 371 (c)(1),
(2) Date: Jan. 26, 2018

(87) PCT Pub. No.: WO2017/019751
PCT Pub. Date: Feb. 2, 2017

(65) Prior Publication Data
US 2018/0363063 A1  Dec. 20, 2018

Related U.S. Application Data

(60) Provisional application No. 62/197,306, filed on Jul. 27, 2016.

(51) Int. Cl.
| | | |
|---|---|---|
| C12Q 1/68 | (2018.01) |
| C12Q 1/6886 | (2018.01) |
| A61B 34/10 | (2016.01) |
| A61B 1/303 | (2006.01) |
| A61B 5/00 | (2006.01) |
| A61N 5/10 | (2006.01) |
| C12N 15/10 | (2006.01) |

(52) U.S. Cl.
CPC ............ *C12Q 1/6886* (2013.01); *A61B 1/303* (2013.01); *A61B 5/0084* (2013.01); *A61B 34/10* (2016.02); *A61N 5/1039* (2013.01); *C12N 15/1093* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 6,492,144 | B1 | 12/2002 | Umansky et al. |
| RE39,920 | E | 11/2007 | Umansky et al. |
| 7,914,982 | B2 | 3/2011 | Melkonyan et al. |
| 7,973,154 | B2 | 7/2011 | Melkonyan et al. |
| 8,383,335 | B2 | 2/2013 | Melkonyan et al. |
| 8,431,123 | B2 | 4/2013 | Genkin et al. |
| 8,486,626 | B2 | 7/2013 | Umansky et al. |
| 8,542,261 | B2 | 9/2013 | Iguchi et al. |
| 8,580,516 | B2 | 11/2013 | Schwartz et al. |
| 8,642,261 | B2 | 2/2014 | Melkonyan et al. |

FOREIGN PATENT DOCUMENTS

WO   2010051261 A3   12/2010

OTHER PUBLICATIONS

Brebi et al Epigenetics. 9:308-317 and Supplemental Material pp. 1-27, Feb 1, 2014.*
Brebi, et al., Genome-wide methylation profiling reveals Zinc finger protein 516 (ZNF516) and FK-506-binding protein 6 (FKBP6) promoters frequently methylated in cervical neoplasia, associated with HPV status and ethnicity in a Chilean population. Epigenetics : official journal of the DNA Methylation Society 9, 308 (Feb 1, 2014).
Lorincz, et al. HPV16 L1 and L2 DNA methylation predicts high-1-16 grade cervical intraepithelial neoplasia in women with mildly abnormal cervical cytology, Int. J. Cancer, 2013, vol. 133, pp. 637-645.
Elshimali, et al. The Clinical Utilization of Circulating Cell Free 1-3, 10 DNA (CCFDNA) in Blood of Cancer Patients. Int. J. Mol. Sci., 2013, vol. 14, pp. 18925-18958.
Gage, et al., The low risk of precancer after a screening result of human papillomavirus-negative/atypical squamous cells of undetermined significance papanicolaou and implications for clinical management. Cancer cytopathology, (Jul. 9, 2014).
Shiffman, et al., Human papillomavirus testing in the prevention of cervical cancer. Journal of the National Cancer Institute 103, 368 (Mar. 2, 2011).
Ho, et al., Natural history of cervicovaginal papillomavirus infection in young women. The New England journal of medicine 338, 423 (Feb. 12, 1998).
McCredie, et al., Natural history of cervical neoplasia and risk of invasive cancer in women with cervical intraepithelial neoplasia 3: a retrospective cohort study. The lancet oncology 9, 425 (May, 2008).
Cogliano, et al., Carcinogenicity of human papillomaviruses. The lancet oncology 6, 204 (Apr. 2005).
Castle, et al., The clinical meaning of a cervical intraepithelial neoplasia grade 1 biopsy. Obstetrics and gynecology 118, 1222 (Dec. 2011).
Gage, et al., Comparison of the co bas Human Papillomavirus (HPV) test with the hybrid capture 2 and linear array HPV DNA tests. Journal of clinical microbiology 50, 61 (Jan. 2012).

(Continued)

*Primary Examiner* — Carla J Myers
(74) *Attorney, Agent, or Firm* — John Hopkins Technology Ventures

(57) ABSTRACT

Methods and kits for triaging a human papillomavirus (HPV)-positive woman into colposcopy are disclosed. The methods comprise determining the promoter methylation level of the promoter regions of a group of genes (e.g., viral and host genes) that exhibit increased promoter methylation in women having CIN2+ lesions as compared to women having no intraepithelial lesions or malignancy (NILM).

16 Claims, 19 Drawing Sheets

Specification includes a Sequence Listing.

(56) References Cited

OTHER PUBLICATIONS

Saslow, et al., American Cancer Society, American Society for Colposcopy and Cervical Pathology, and American Society for Clinical Pathology screening guidelines for the prevention and early detection of cervical cancer. Americanjournal of clinical pathology 137, 516 (Apr. 2012).
Katki, et al., Five-year risks of CIN 3+ and cervical cancer among women who test Pap-negative but are HPV-positive. Journal of lower genital tract disease 17, S56 (Apr. 2013).
Massad, et al., 2012 updated consensus guidelines for the management of abnormal cervical cancer screening tests and cancer precursors. Obstetrics and gynecology 121, 829 (Apr. 2013).
Gage, et al., Reassurance against future risk of precancer and cancer conferred by a negative human papillomavirus test. Journal of the National Cancer Institute 106 (Aug. 2014).
Katki, et al., Five-year risk of recurrence after treatment of CIN 2, CIN 3, or AIS: performance of HPV and Pap cotesting in posttreatment management. Journal of lower genital tract disease 17, S78 (Apr. 2013).
Schiffman, et al., Human papillomavirus infection and the multistage carcinogenesis of cervical cancer. Cancer epidemiology, biomarkers & prevention : a publication of the American Association for Cancer Research, cosponsored by the American Society of Preventive Oncology 22, 553 (Apr. 2013).
Fernandez, et al., The dynamic DNA methylomes of double-stranded DNA viruses associated with human cancer. Genome research 19, 438 (Mar. 2009).
Mirabello, et al., Elevated methylation of HPV16 DNA is associated with the development of high grade cervical intraepithelial neoplasia. International journal of cancer. Journal international du cancer 132, 1412 (Mar. 15, 2013).
Wentzensen, et al., Methylation of HPV18, HPV31, and HPV45 genomes and cervical intraepithelial neoplasia grade 3. Journal of the National Cancer Institute 104, 1738 (Nov. 21, 2012).
Mirabello, et al., Methylation of human papillomavirus type 16 genome and risk of cervical precancer in a Costa Rican population. Journal of the National Cancer Institute 104, 556 (Apr. 4, 2012).
Sun, et al., Methylation of HPV16 genome CpG sites is associated with cervix precancer and cancer. Gynecologic oncology 121, 59 (Apr. 2011).
Vasiljevic, et al., A comparison of methylation levels in HPV18, HPV31 and HPV33 genomes reveals similar associations with cervical precancers. Journal of clinical virology: the ofjicial publication of the Pan American Society for Clinical Virology 59, 161 (Mar. 2014).
Vasiljevic, et al., Credentialing of DNA methylation assays for human genes as diagnostic biomarkers of cervical intraepithelial neoplasia in high-risk HPV positive women. Gynecologic oncology 132, 709 (Mar. 2014).
Lendvai, et al., Genome-wide methylation profiling identifies hypemiethylated biomarkers in high-grade cervical intraepithelial neoplasia. Epigenetics : ofjicial journal of the DNA Methylation Society 7, 1268 (Nov. 2012).
Eijsink, et al., A four-gene methylation marker panel as triage test in highrisk human papillomavirus positive patients. International journal of cancer. Journal international du cancer 130, 1861(Apr. 15, 2012).
Krueger, et al., Bismark: a flexible aligner and methylation caller for Bisulfite-Seq applications. Bioinformatics 27, 1571 (Jun. 1, 2011).
Brentnall, et al., A DNA methylation classifier of cervical precancer based on human papillomavirus and human genes. International journal of cancer. Journal international du cancer 135, 1425 (Sep. 15, 2014).
Mendez, et al., Urine-based human papillomavirus DNA testing as a screening tool for cervical cancer in high-risk women. International journal of gynaecology and obstetrics: the official organ of the International Federation of Gynaecology and Obstetrics 124, 151 (Feb. 2014).
Sahasrabuddhe, et al., Comparison of human papillomavirus detections in urine, vulvar, and cervical samples from women attending a colposcopy clinic. Journal of clinical microbiology 52, 187 (Jan. 2014).
Payan, et al., Human papillomavirus quantification in urine and cervical samples by using the Mx4000 and LightCycler general real-time PCR systems. Journal of clinical microbiology 45, 897 (Mar. 2007).
Vorsters, et al., Optimization of HPV DNA detection in urine by improving collection, storage, and extraction. European journal of clinical microbiology & infectious diseases: official publication of the European Society of Clinical Microbiology, (Jun. 12, 2014).
Vorsters, et al., Detection of human papillomavirus DNA in urine. A review of the literature. European journal of clinical microbiology & infectious diseases: official publication of the European Society of Clinical Microbiology 31, 627 (May 2012).
Ducancelle, et al., Interest of Human Papillomavirus DNA quantification and genotyping in paired cervical and urine samples to detect cervical lesions. Archives of gynecology and obstetrics, (Mar. 13, 2014).
Lichtenstein, et al., Circulating nucleic acids and apoptosis. Annals of the New York Academy of Sciences 945, 239 (Sep. 2001).
Su, et al., Transrenal DNA as a diagnostic tool: important technical notes. Annals of the New York Academy of Sciences 1022, 81 (Jun. 2004).
Shekhtman, et al., Optimization of transrenal DNA analysis: detection of fetal DNA in maternal urine. Clinical chemistry 55, 723 (Apr. 2009).
Melkonyan, et al., Transrenal nucleic acids: from proof of principle to clinical tests. Annals of the New York Academy of Sciences 1137, 73 (Aug. 2008).
Cannas, et al., Mycobacterium tuberculosis DNA detection in soluble fraction of urine from pulmonary tuberculosis patients. The international journal of tuberculosis and lung disease : the official journal of the International Union against Tuberculosis and Lung Disease 12, 146 (Feb. 2008).
Sahasrabuddhe, et al., Evaluation of clinical performance of a novel urine-based HPV detection assay among women attending a colposcopy clinic. Journal of clinical virology : the official publication of the Pan American Society for Clinical Virology, (May 2, 2014).
Steinau, et al., Performance of commercial reverse line blot assays for human papillomavirus genotyping. Journal of clinical microbiology 50, 1539 (May 2012).
Park, et al., Characterization of the methylation patterns in human papillomavirus type 16 viral DNA in head and neck cancers. Cancer prevention research 4, 207 (Feb. 2011).
Langmead, et al., Fast gapped-read alignment with Bowtie 2. Nature methods 9, 357 (Apr. 2012).
Altschul, et al., Gapped Blast and Psi-Blast: anew generation of protein database search programs. Nucleic acids research 25, 3389 (Sep. 1, 1997).
Thompson, et al., The ENIGMA Consortium: large-scale collaborative analyses of neuroimaging and genetic data. Brain imaging and behavior 8, 153 (Jun. 2014).
Beaudenon, et al., HPV E6, E6AP and cervical cancer. BMC Biochem 9 Suppl 1, S4 (2008).
Dehn, et al., Human papillomavirus testing and molecular markers of cervical dysplasia and carcinoma. Cancer 111, 1 (Feb. 25, 2007).
Kjaer, et al., Type specific persistence of high risk human papillomavirus (HPV) as indicator of high grade cervical squamous intraepithelial lesions in young women: population based prospective follow up study. BMJ325, 572 (Sep. 14, 2002).
Monsonego, et al., Cervical cancer control, priorities and new directions. Int J Cancer 108, 329 (Jan. 20, 2004).
Cuschieri, et al., Human papillomavirus type specific DNA and RNA persistence—implications for cervical disease progression and monitoring. J Med Virol 73, 65 (May 2004).
Brown, et al., New technologies for cervical cancer screening. Best practice & research. Clinical obstetrics & gynaecology 26, 233 (Apr. 2012).
Van Doorslaer, et al., The Papillomavirus Episteme: a central resource for papillomavirus sequence data and analysis. Nucleic acids research 41, D571 (Jan. 2013).

(56) References Cited

OTHER PUBLICATIONS

Walenz, et al., Sim4db and Leaff: utilities for fast batch spliced alignment and sequence indexing. Bioinformatics 27, 1869 (Jul. 1, 2011).

* cited by examiner

SEQUENCE LISTING

```
<160> NUMBER OF SEQ ID NOS: 12

<210> SEQ ID NO 1
<211> LENGTH: 24
<212> TYPE: DNA
<213> ORGANISM: Human papillomavirus type 16

<400> SEQUENCE: 1
tatagcggtt ggtttgggtt tgtg                                           24

<210> SEQ ID NO 2
<211> LENGTH: 25
<212> TYPE: DNA
<213> ORGANISM: Human papillomavirus type 16

<400> SEQUENCE: 2
acattctcta ttatccacac ctaca                                          25

<210> SEQ ID NO 3
<211> LENGTH: 21
<212> TYPE: DNA
<213> ORGANISM: Artificial Sequence
<220> FEATURE:
<223> OTHER INFORMATION: synthetic sequence

<400> SEQUENCE: 3
aggtgttgag gtaggtcgtg g                                              21

<210> SEQ ID NO 4
<211> LENGTH: 20
<212> TYPE: DNA
<213> ORGANISM: Artificial Sequence
<220> FEATURE:
<223> OTHER INFORMATION: synthetic sequence

<400> SEQUENCE: 4
atatttcgta ttttatcgcg                                                20
```

<210> SEQ ID NO 5
<211> LENGTH: 18
<212> TYPE: DNA
<213> ORGANISM: Artificial Sequence
<220> FEATURE:
<223> OTHER INFORMATION: synthetic sequence

<400> SEQUENCE: 5
atcgtttcgt tccaaccg                                                   18

<210> SEQ ID NO 6
<211> LENGTH: 24
<212> TYPE: DNA
<213> ORGANISM: Artificial Sequence
<220> FEATURE:
<223> OTHER INFORMATION: synthetic sequence

<400> SEQUENCE: 6
cgaccctaac cctcgcgaac tcta                                            24

<210> SEQ ID NO 7
<211> LENGTH: 19
<212> TYPE: DNA
<213> ORGANISM: Artificial Sequence
<220> FEATURE:
<223> OTHER INFORMATION: synthetic sequence

<400> SEQUENCE: 7
acggtgaggt atgtatacg                                                  19

<210> SEQ ID NO 8
<211> LENGTH: 19
<212> TYPE: DNA
<213> ORGANISM: Artificial Sequence
<220> FEATURE:
<223> OTHER INFORMATION: synthetic sequence

<400> SEQUENCE: 8
actcgaaacc ctcaaaacg                                                  19

<210> SEQ ID NO 9
<211> LENGTH: 24
<212> TYPE: DNA
<213> ORGANISM: Artificial Sequence
<220> FEATURE:
<223> OTHER INFORMATION: synthetic sequence

<400> SEQUENCE: 9
aacgccaaac ctcaccgtcg tacg                                            24

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10 cgttttcgt cgtcgtttta                                                  20

<210> SEQ ID NO 11
<211> LENGTH: 23
<212> TYPE: DNA
<213> ORGANISM: Artificial Sequence
<220> FEATURE:

```
<223> OTHER INFORMATION: synthetic sequence

<400> SEQUENCE: 11
aaacaaaaaa aataaccgac gat                                        23

<210> SEQ ID NO 12
<211> LENGTH: 24
<212> TYPE: DNA
<213> ORGANISM: Artificial Sequence
<220> FEATURE:
<223> OTHER INFORMATION: synthetic sequence

<400> SEQUENCE: 12
tataacctcc gccctccctc ccta                                       24
```

METHOD TO USE VIRAL AND HOST METHYLATION MARKERS FOR CERVICAL CANCER SCREENING AND TRIAGE IN LIQUID PREP, SERUM/PLASMA, AND URINE: PCR AND SEQUENCING BASED PROCESS METHODS

CROSS-REFERENCE TO RELATED APPLICATIONS

This application is a 35 U.S.C. § 371 U.S. national entry of International Application PCT/US2016/044225, having an international filing date of Jul. 27, 2016, which claims the benefit of U.S. Provisional Application No. 62/197,306, filed Jul. 27, 2015, the content of each of the aforementioned applications is herein incorporated by reference in their entirety.

FEDERALLY SPONSORED RESEARCH OR DEVELOPMENT

This invention was made with government support under grant numbers CA084986, and CA164092, awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "P13649-03_ST25". The sequence listing is 2,335 bytes in size, and was created on Aug. 2, 2018. It is hereby incorporated by reference in its entirety.

BACKGROUND

Cervical cancer screening is undergoing a major transformation with the adoption of testing for the presence of oncogenic human papilloma virus (HPV) types (1, 2). Persistent HPV infection of the cervical epithelium is a rare event because most infections are usually cleared without treatment (3). Yet a small percentage of HPV infections are associated to progression from low-grade squamous intraepithelial lesions (LSIL) to cervical intraepithelial neoplasia grade 3 (CIN3) lesions (4). In fact, persistent infection with at least one of the 13 carcinogenic types from the *alphapapillomavirus* genus (HPV16, 18, 31, 33, 35, 39, 45, 51, 52, 56, 58, 59, 68) has been linked to cervical cancer (5). Close to 30% of CIN3 lesions progress to cervical cancer, but there are no agreed upon clinical tests of progression to cervical cancer (6, 7).

The new cervical cancer screening guidelines in the United States recommend HPV co-testing with Pap among women 30 years and older (8). However, clinical management for HPV-positive/Pap-negative women is not firmly established (9, 10). HPV has recently been shown to be a better indicator of cervical cancer risk than the Pap test (11). But even when co-testing with Pap and HPV has higher sensitivity and specificity than each separate test, together they cannot predict who will progress to cervical carcinoma (12, 13).

This led to the search of molecular markers of risk to progression to cervical cancer. HPV DNA methylation, like other DNA viruses, is correlated to progression to cancer (14). This seminal finding led to subsequent studies suggesting that detection of methylated HPV DNA may distinguish women with cervical intraepithelial neoplasia grade 2-3 (CIN2+) from women with an oncogenic HPV type infection who show no evidence of CIN2+ (15-19). In parallel, other groups examined the association between host DNA methylation and cervical cancer (20-23). Recent studies, have reported a positive association between CIN2+ and methylation of CpG sites in host and viral DNA isolated from liquid cytology samples (19, 20, 24).

Recently published reports have also explored the use of urine-based high risk HPV testing, as an alternative approach to liquid cytology for cervical cancer screening, in an attempt to identify less invasive cervical cancer screening technologies (25-27). Most of the studies have failed to attain clinical usefulness as they are limited by poor sensitivity, inappropriate protocols for DNA extraction from circulating DNA in urine, small sample size, and the limit of detection of the HPV assays utilized (28-30). Most of the studies also fail to recognize the importance of using DNA isolation methods optimized to enrich for fragmented circulating cell-free DNA (ccfDNA) that crosses the kidneys and can be obtained in urine (31).

There is growing evidence that circulating short human, viral, and bacterial DNA fragments from dying cells throughout the body, approximately 150-250 bases long on average, pass through the renal barrier and appear in urine as Transrenal DNA (TrDNA)(32) or ccfDNA. ccfDNA has been proposed as a tool for non-invasive prenatal monitoring, infectious disease monitoring, and tumor response monitoring (33-35). Recently, a capillary electrophoresis ccfDNA test that targets the E1 region of the HPV genome for the detection of high risk HPV demonstrated high sensitivity and modest specificity for urine-based detection of cervical pre-cancerous lesions (36).

Urine samples tested by the ccfDNA HPV capillary electrophoresis test had high concordance with corresponding cervical and urine samples tested by the widely used Linear Array HPV Genotyping Test (LA-HPV)(37). However, the ccfDNA capillary electrophoresis HPV test is not quantitative, can only detect the presence or absence of high risk HPV and, similar to previously published urine based HPV tests, has limited specificity. None of the high-risk HPV urine-based reports use sequencing based approaches to quantify multiple HPV types, nor include methylated markers in their workflow to improve the sensitivity and specificity of the ccfDNA test.

SUMMARY

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science, and Current Protocols in Cell Biology*, all John Wiley & Sons, N.Y., edition as of December 2008; Sambrook, Russell, and Sambrook, *Molecular Cloning. A Laboratory Manual*, 3$^{rd}$ ed., Cold Spring Harbor Laboratory Press, Cold Spring Harbor, 2001; Harlow, E. and Lane, D., *Antibodies—A Laboratory Manual*, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

In an aspect, the presently disclosed subject matter provides a method for triaging a human papillomavirus (HPV)-positive woman into colposcopy, the method comprising: (a) selecting a HPV-positive woman testing positive for one or more high risk types of HPV; (b) obtaining nucleic acid from a test sample from the selected HPV-positive woman; (c) determining in the nucleic acid from the test sample of the selected HPV-positive woman a promoter methylation level of the promoter regions of a group of genes that exhibit increased promoter methylation in women having CIN2+ lesions as compared to women having no intraepithelial lesions or malignancy (NILM); and (d) triaging the HPV-positive woman into colposcopy when the level of promoter methylation of the group of genes is increased relative to the level of promoter methylation of the group of genes in a reference sample obtained from women having NILM.

In an aspect, the presently disclosed subject matter provides a method for triaging a human papillomavirus (HPV)-positive woman into colposcopy, the method comprising: (a) selecting a HPV-positive woman testing positive for one or more high risk types of HPV; (b) providing a kit that comprises the probes and/or primers needed for determining in the nucleic acid from a test sample of the selected HPV-positive woman a promoter methylation level of the promoter regions of a group of genes that exhibit increased promoter methylation in women having CIN2+ lesions as compared to women having no intraepithelial lesions or malignancy (NILM); (c) obtaining nucleic acid from the test sample from the selected HPV-positive woman; (d) determining the promoter methylation level in the nucleic acid from the test sample of the selected HPV-positive woman using the provided kit; and (e) triaging the HPV-positive woman into colposcopy when the level of promoter methylation of the group of genes is increased relative to the level of promoter methylation of the group of genes in a reference sample obtained from women having NILM.

In an aspect, the presently disclosed subject matter provides a kit for triaging a human papillomavirus (HPV)-positive woman into colposcopy, the kit comprising: (a) a container containing primers and/or probes specific for a group of genes that exhibit increased promoter methylation in women having CIN2+ lesions as compared to women having no intraepithelial lesions or malignancy (NILM); and (b) instructions for use of the primers and/or probes in triaging a human papillomavirus (HPV)-positive woman into colposcopy.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
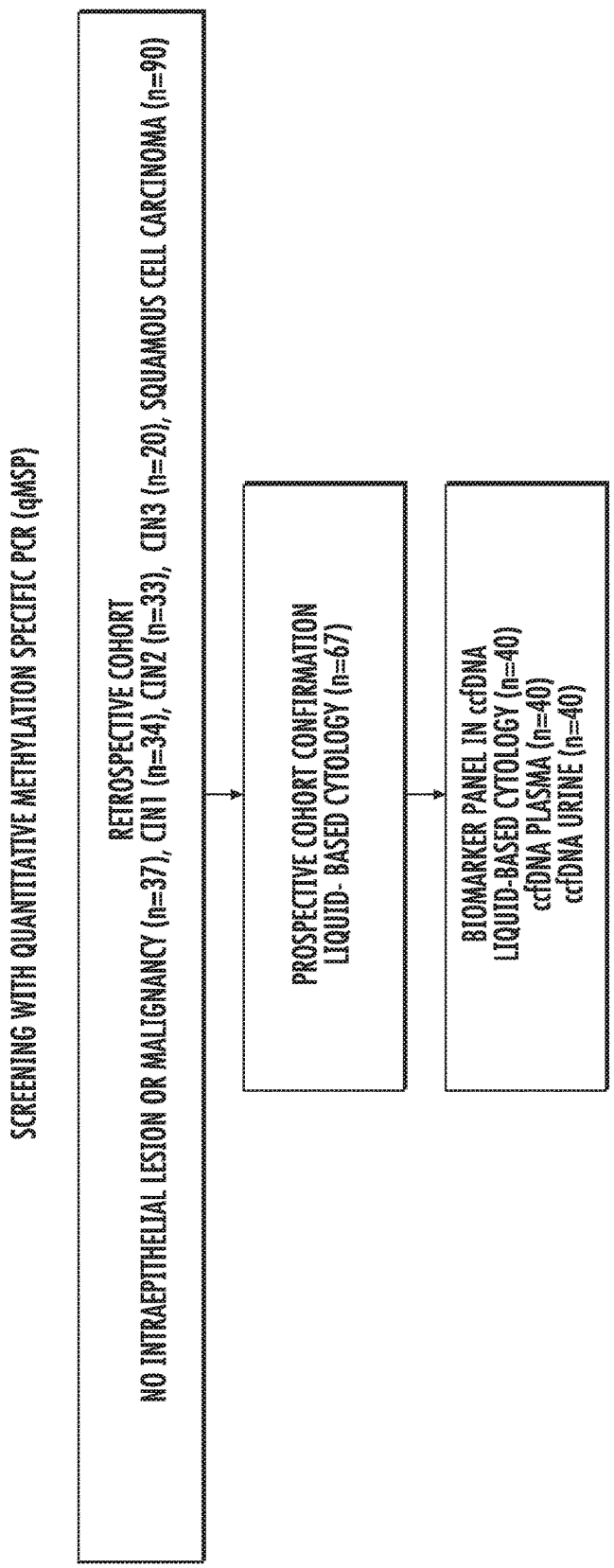
Figure 1A:
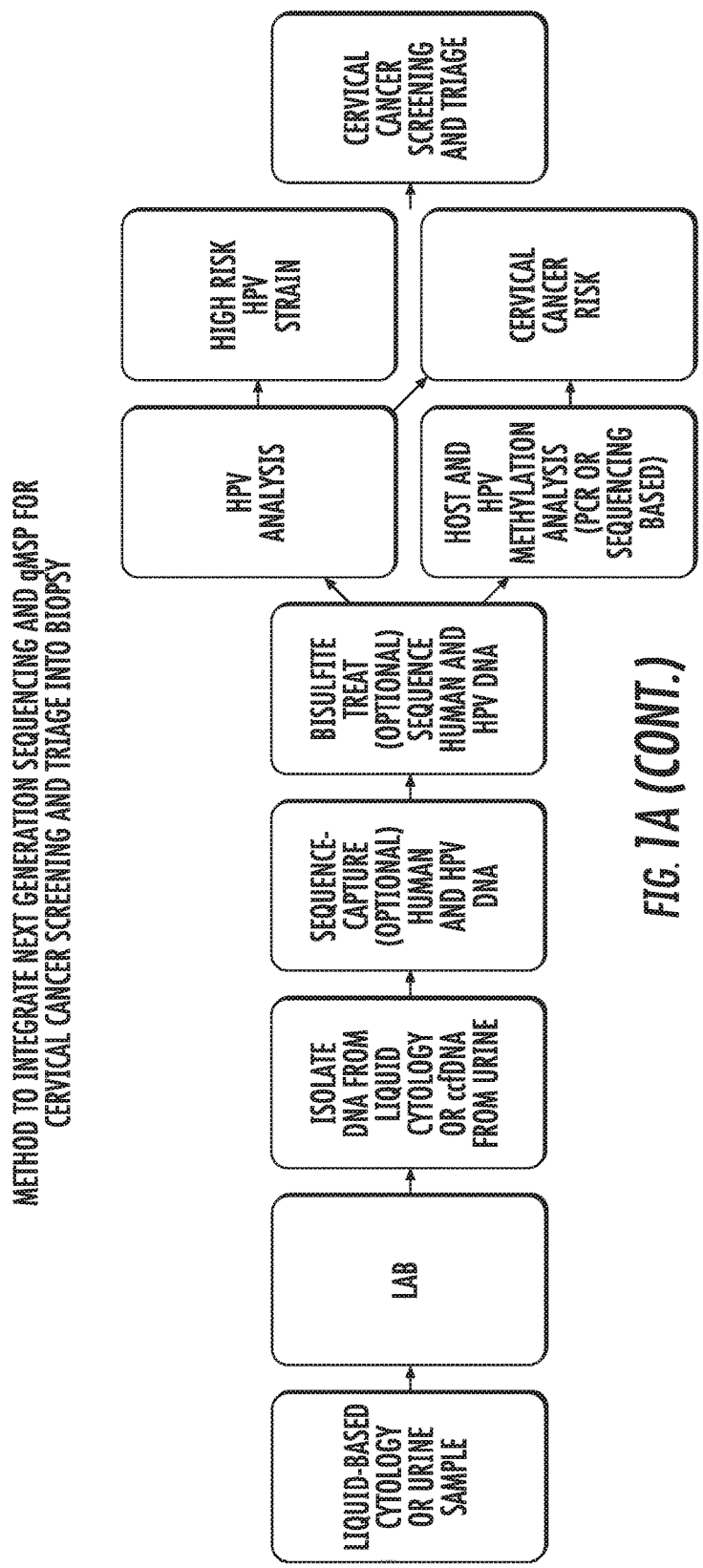
Figure 1B:
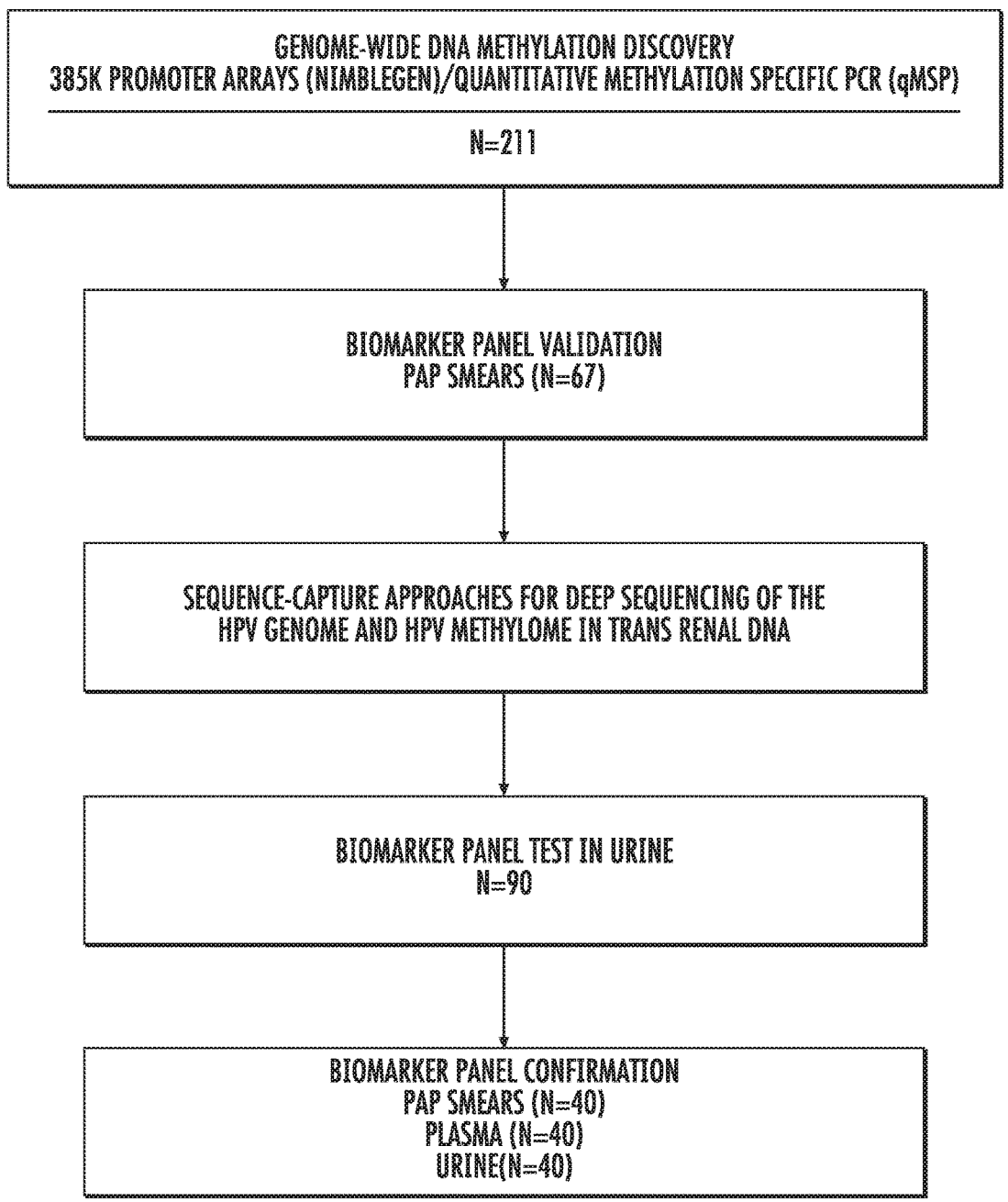
Figure 2A:
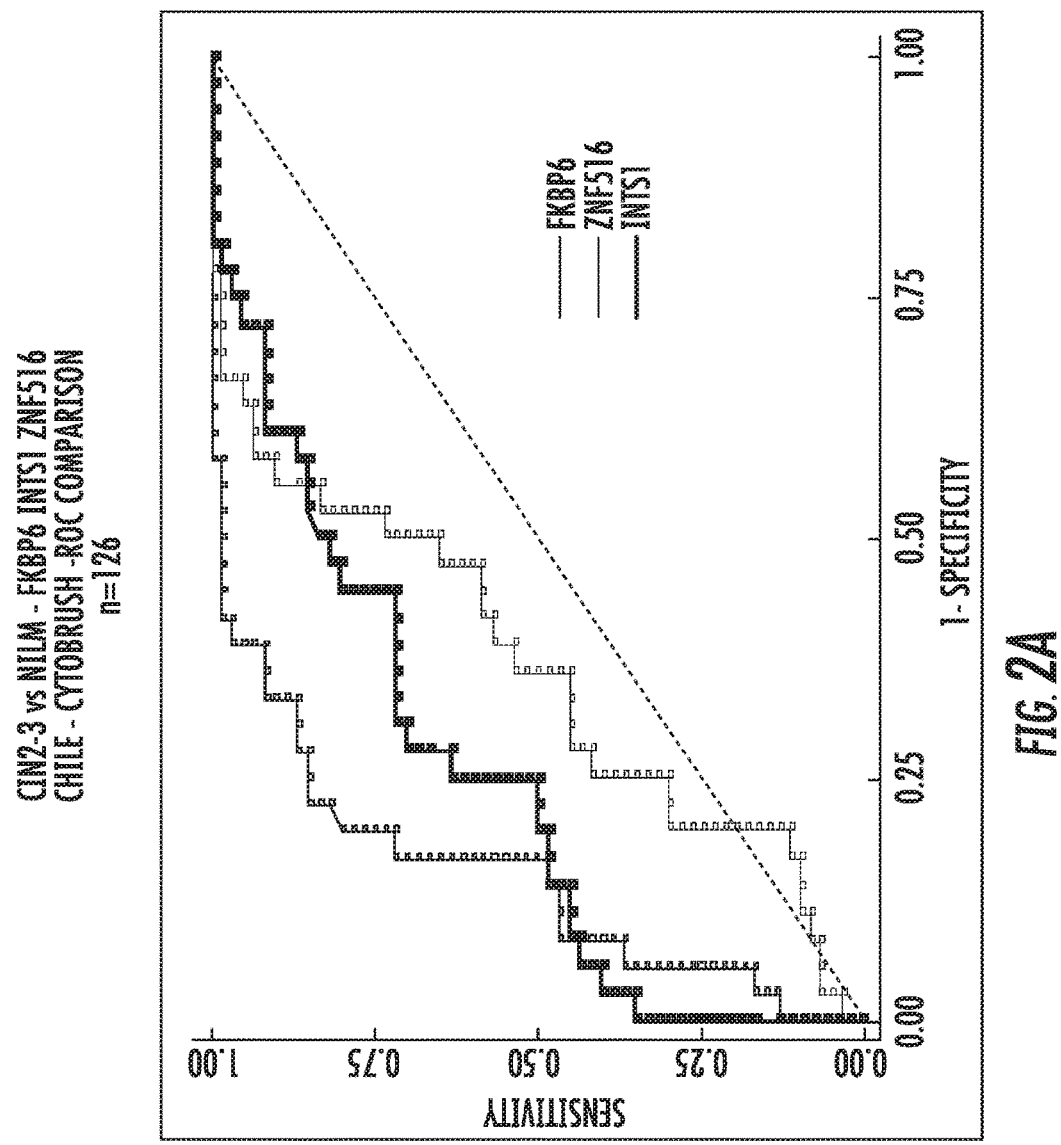
Figure 2B:
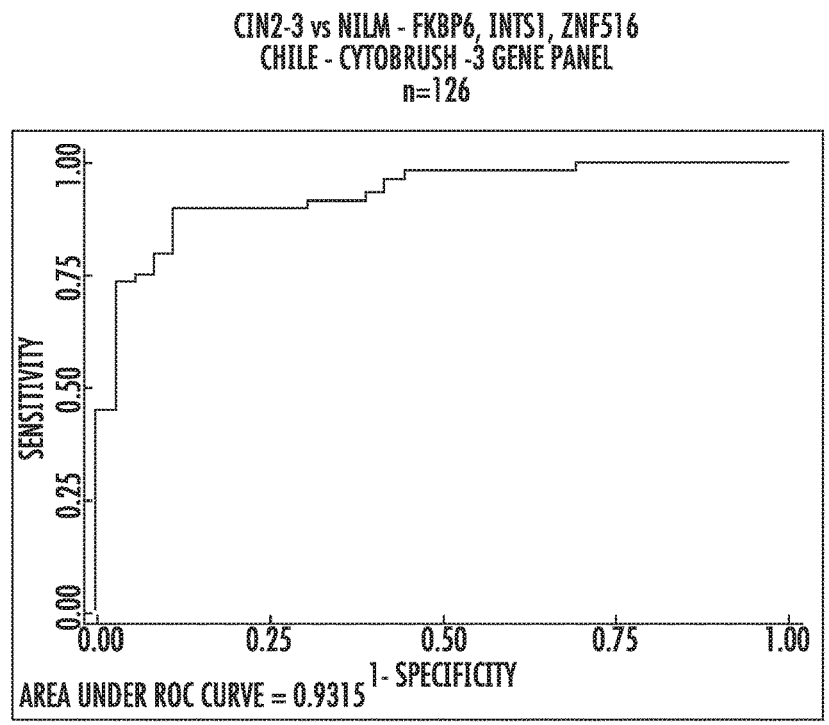
Figure 3A:
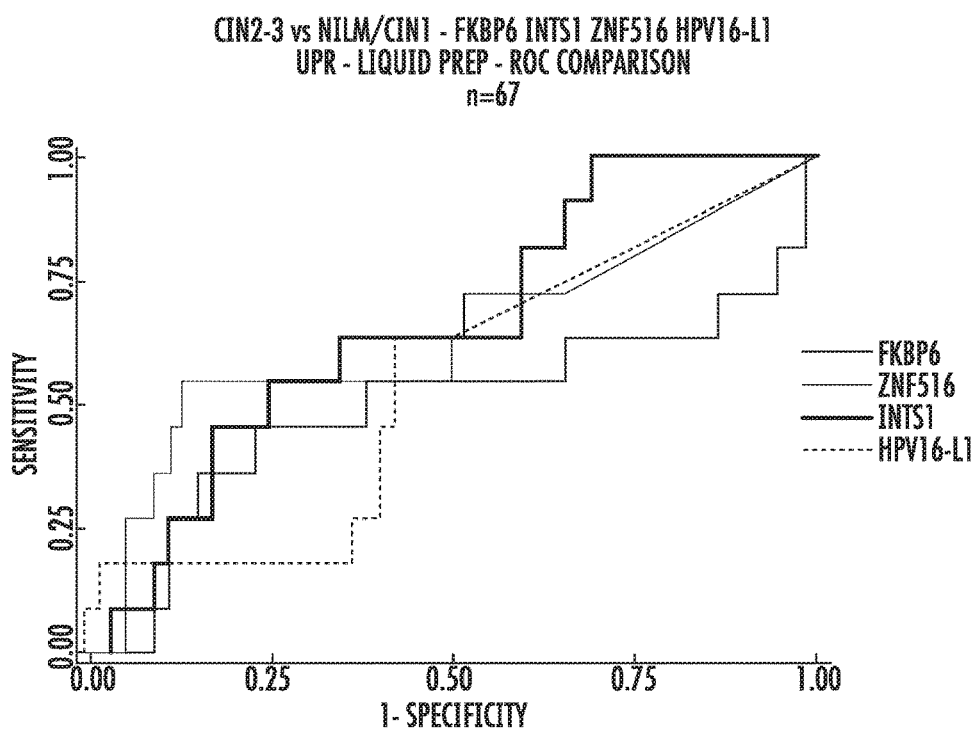
Figure 3B:
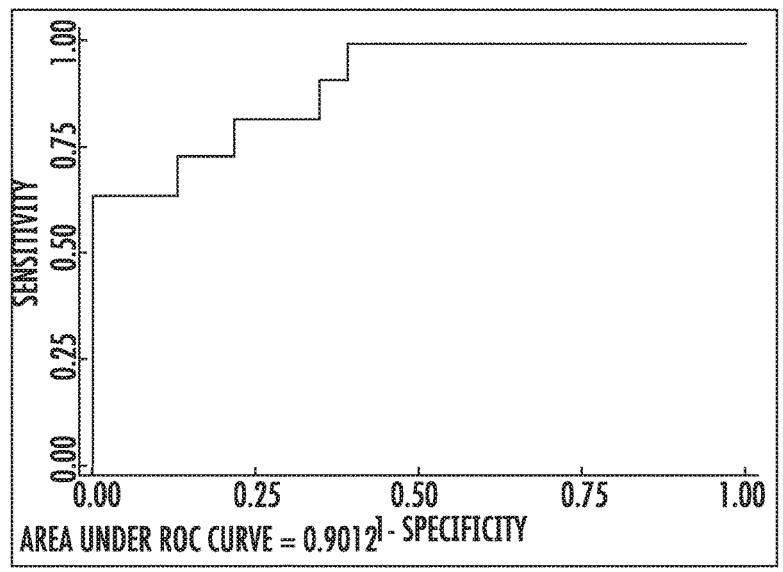
Figure 4:
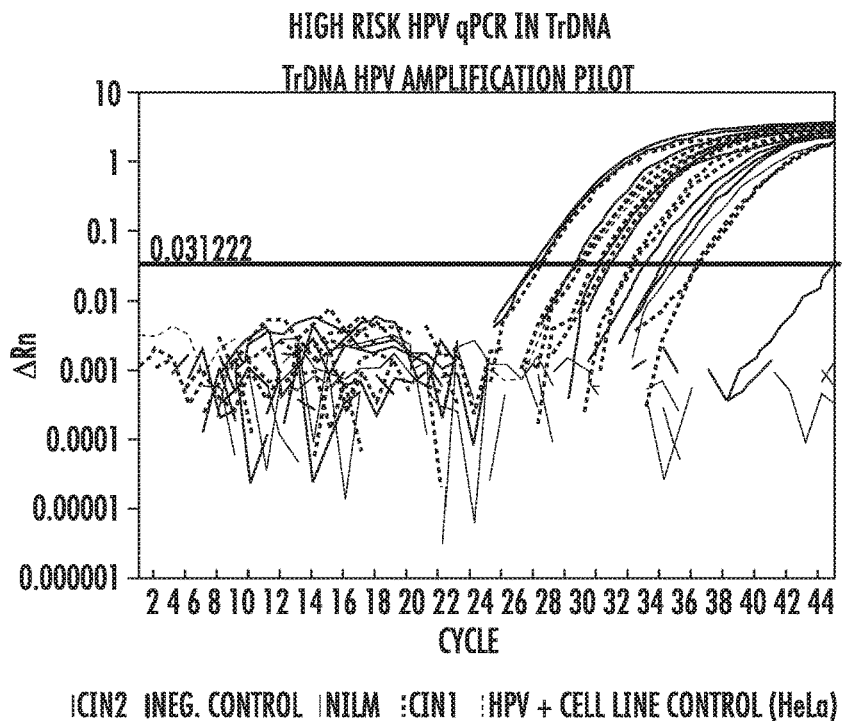
Figure 5A:
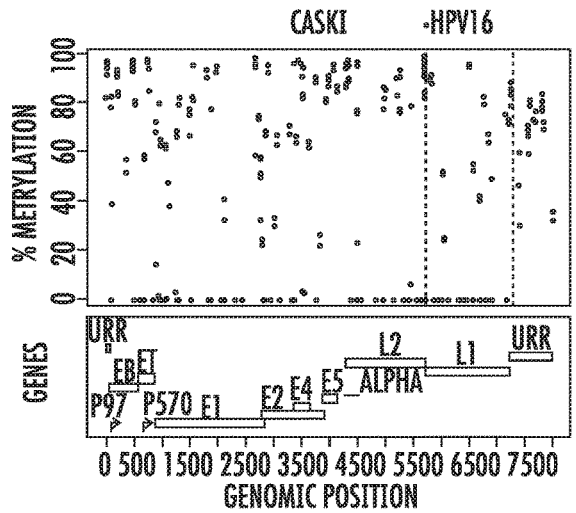
Figure 5B:
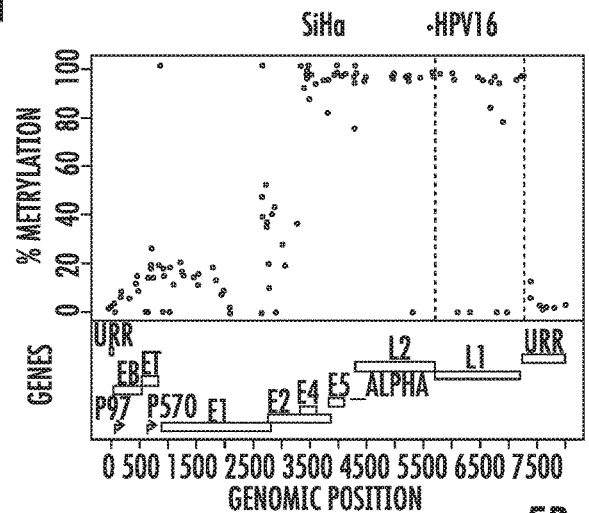
Figure 5C:
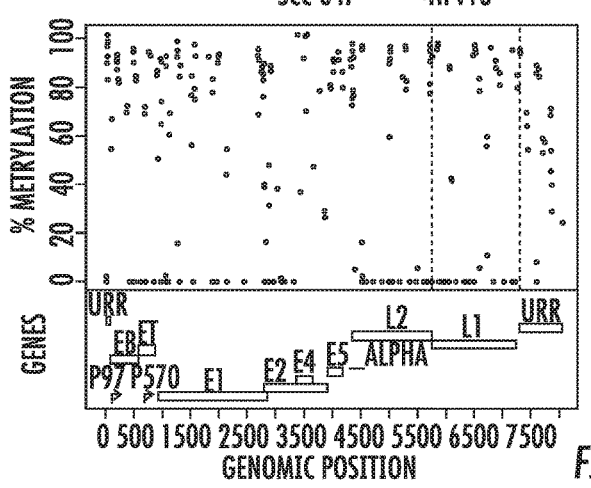
Figure 5D:
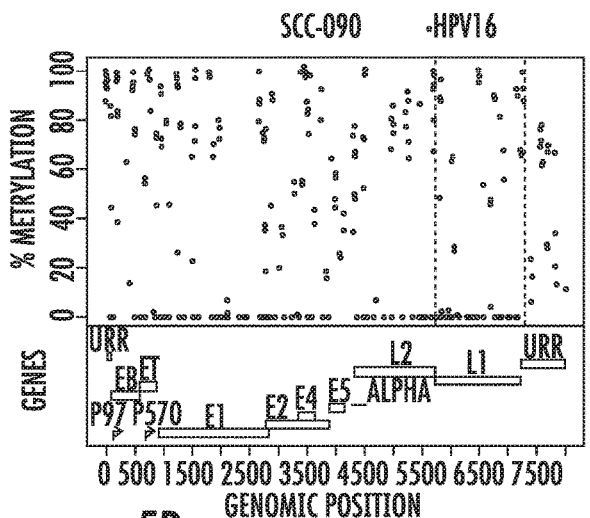
Figure 5E:
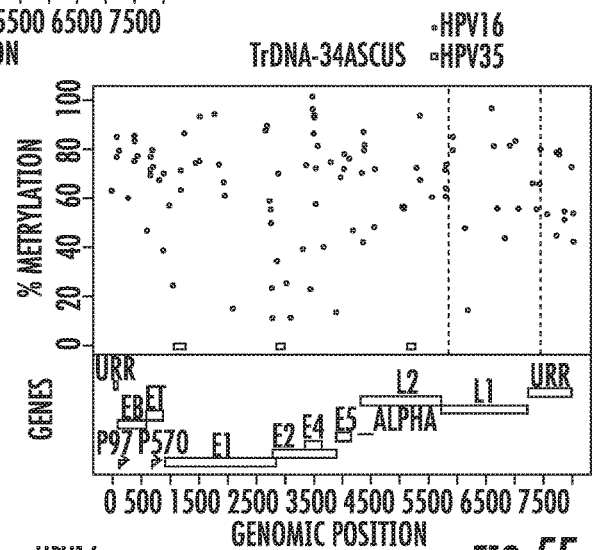
Figure 5F:
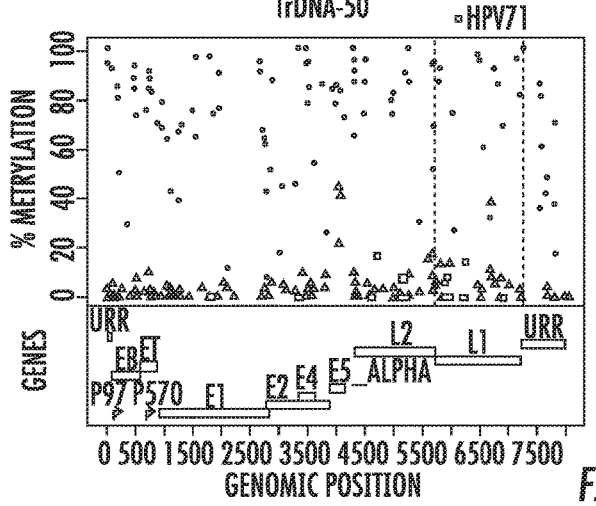

Having thus described the presently disclosed subject matter in general terms, reference will now be made to the accompanying Figures, which are not necessarily drawn to scale, and wherein:

FIG. 1A shows a description of the method used. Exemplary steps 1-9 as shown include liquid prep and or urine sample is collected and sent to the lab, DNA isolation, human and HPV DNA sequence capture, bisulfite treatment of human and HPV DNA (or enzymatic restriction with CG sensitive enzymes), sequencing, HPV genotyping to identify high risk strains, human and HPV DNA methylation analyses to identify differentially methylated regions (DMRs), identify premalignant lesions/assess cervical cancer risk/assess risk of progression to CIN2+, and deliverables: cervical cancer screening and/or triage results. FIG. 1B shows the project workflow, for example, discovery was performed in cervical cancer biopsy samples and cervical brush epithelium from normal controls. Nimblegen 385K CpG plus Promoter oligonucleotide arrays were used to hybridize samples enriched with Methylated DNA Immunoprecipitation (MeDIP). Promoter methylation of ZNF516, INTS1 and FKBP6 discriminated between normal and cancer samples. The panel was Validated on cervical brush samples from patents with Cervical Intraepithelial Neoplasia 2-3 (CIN2+) compared to patents with No Intraepithelial Lesions or Malignancy (NILM) (n=211). Promoter methylation of ZNF516, INTS1 and FKBP6, the host gene panel, together with HPV16-L1 DNA methylation discriminated between CIN2+ and NILM on liquid prep samples (n=67). Custom sequence capture probes were designed to capture the high-risk HPV genome and methylome, before performing library prep for massively parallel Next-Generation Sequencing. The ccfDNA HPV16-L1 methylation is tested in urine, and plasma samples;

FIG. 2A shows ROC curves of FKBP6 INTS1 ZNF516 promoter methylation, comparing CIN2-3 vs NILM in cervical brush samples from Chile (n=126). FIG. 2B shows ROC curve of a combined molecular panel integrated by FKBP6 INTS1 ZNF516 promoter methylation, comparing CIN2-3 vs NILM in cervical brush samples from Chile (n=126);

FIG. 3A shows ROC curves of FKBP6, INTS1, ZNF516 promoter methylation and HPV16-L1 methylation, comparing CIN2-3 vs NILM in liquid-based cytology samples (n=67). FIG. 3B shows ROC curve of a combined molecular panel integrated by FKBP6, INTS1, ZNF516 promoter methylation and HPV16-L1 methylation, comparing CIN2-3 vs NILM in liquid-based cytology samples. (n=67);

FIG. 4 shows amplification curves for the HPV ccfDNA-qPCR assay on ccfDNA from women with Cervical Intraepithelial Neoplasia 1 (CIN1), Cervical Intraepithelial Neoplasia 2-3 (CIN2-3) and women with no Intraepithelial Lesions or Neoplasia (NILM). ccfDNA samples were analyzed for high risk HPV DNA using our HPV ccfDNA SYBR green qPCR assay. HeLa genomic DNA was included as a positive control. Ct ranges are variable, but are in a similar range as the genomic control. NILM samples did not amplify;

FIG. 5 shows sequence capture of methylated high risk HPV.

Figure 6A:
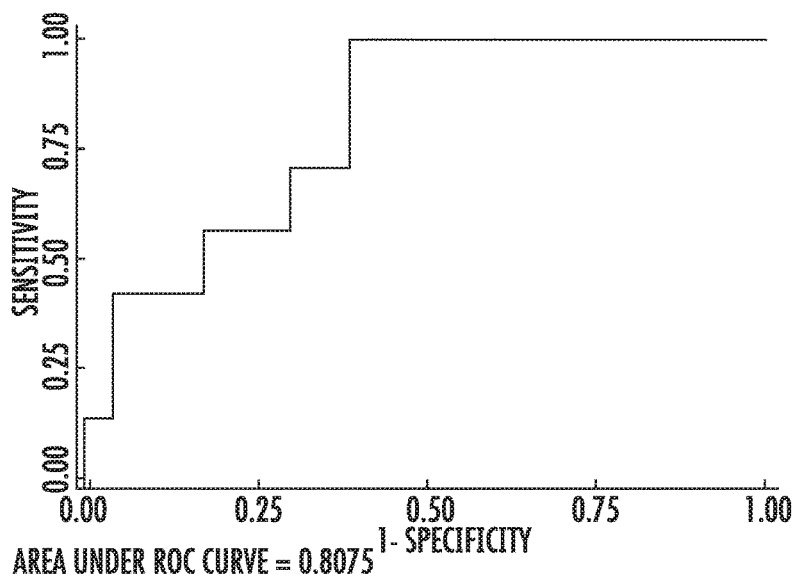
Figure 6B:
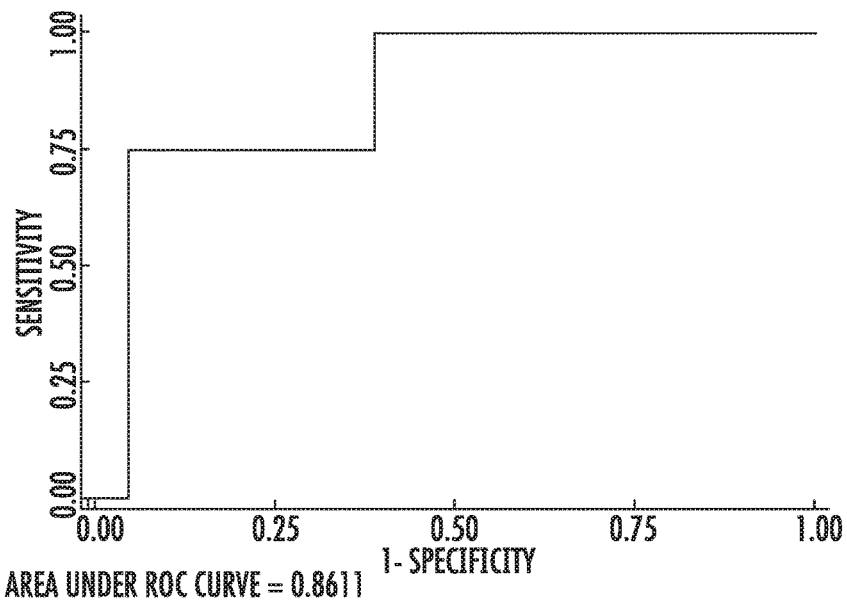
Figure 7:
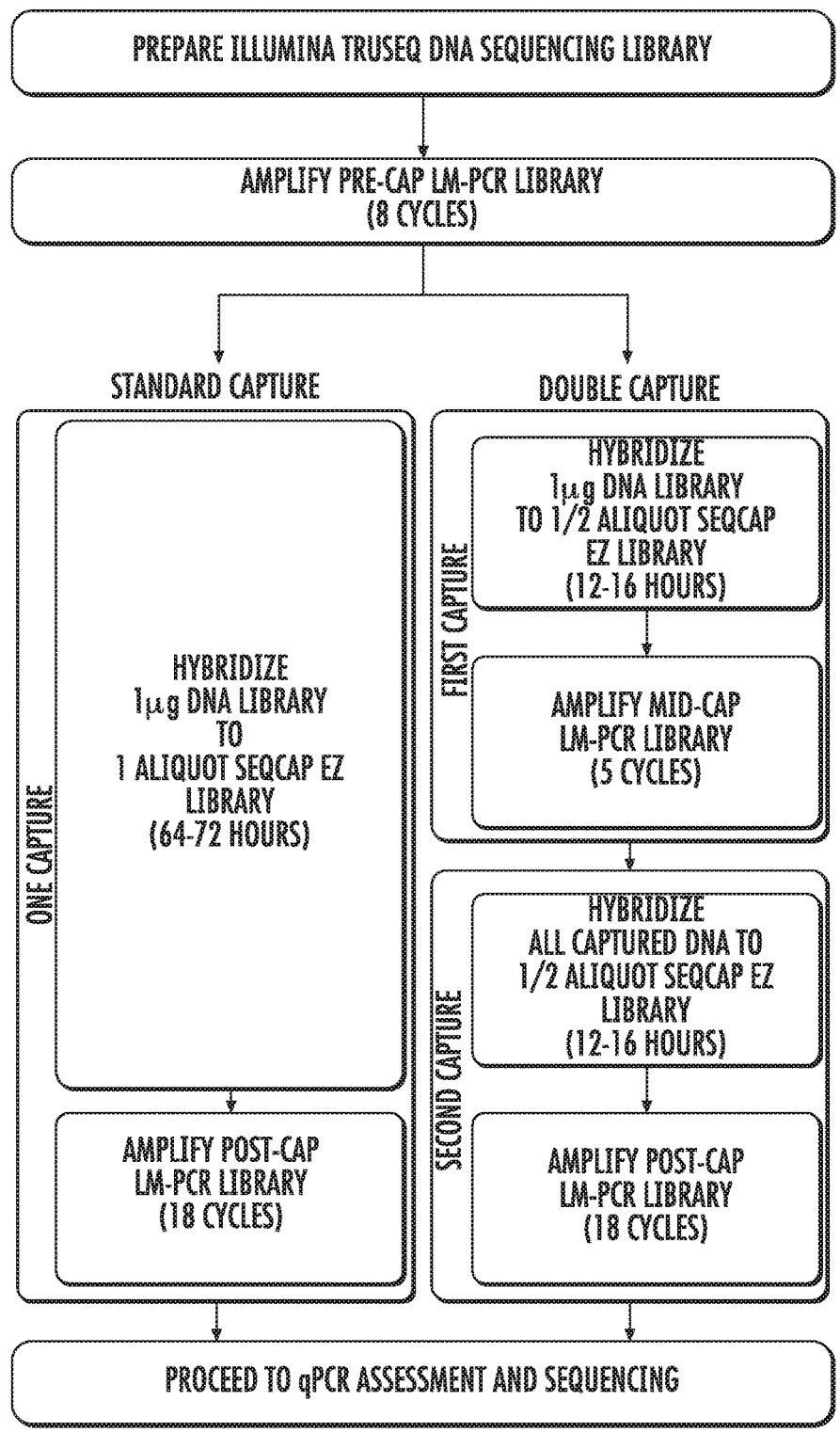
Figure 8:
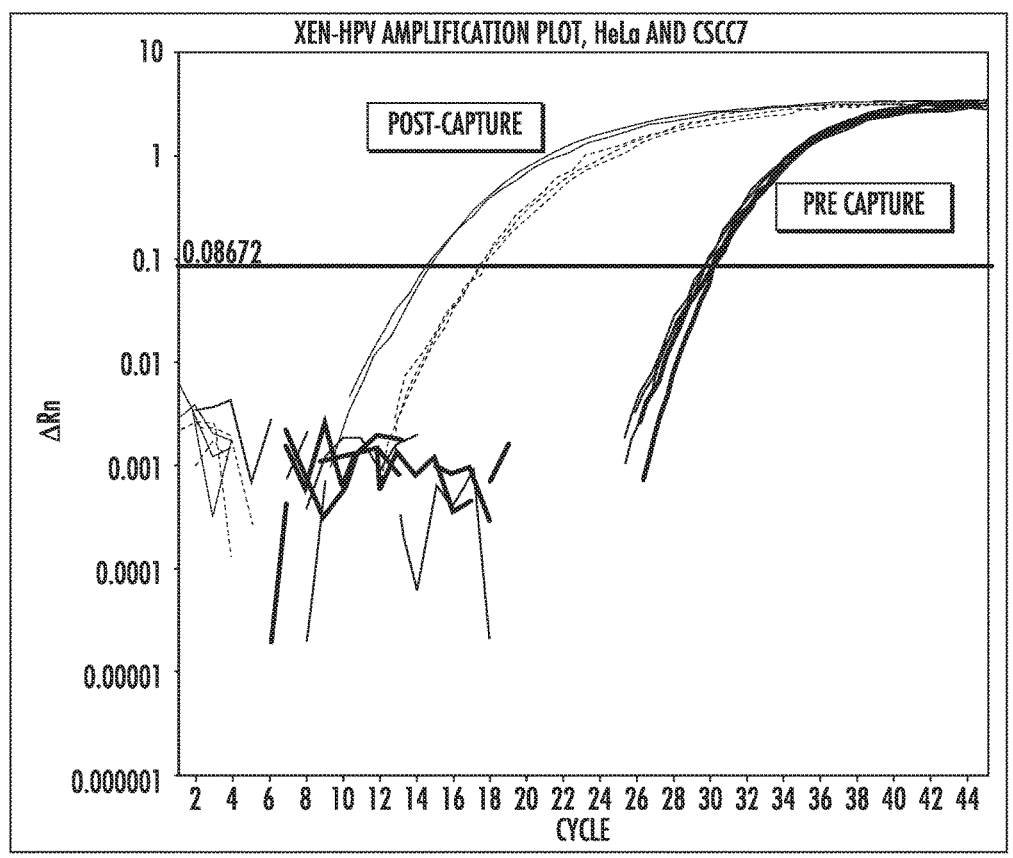
Figure 9:
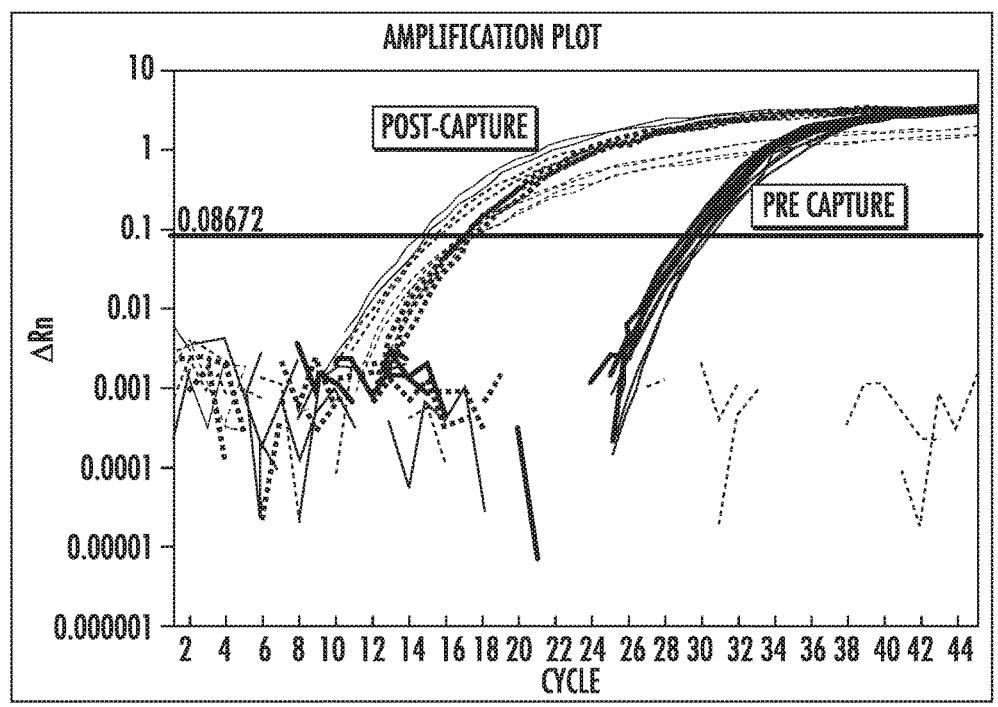
Figure 10:
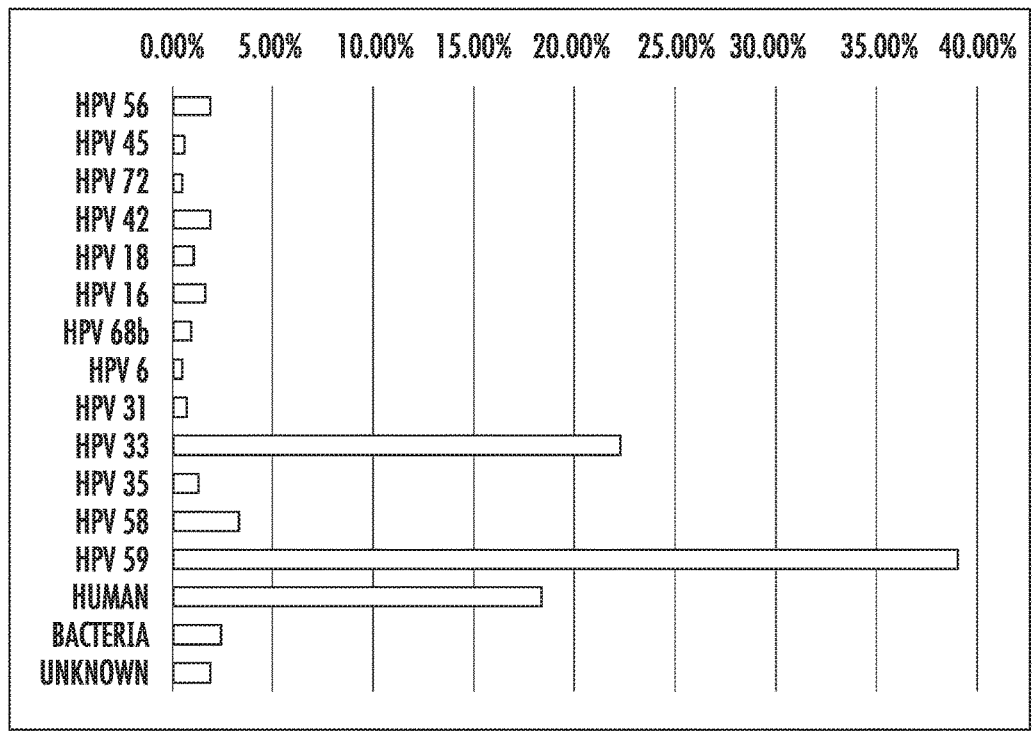
Figure 11:
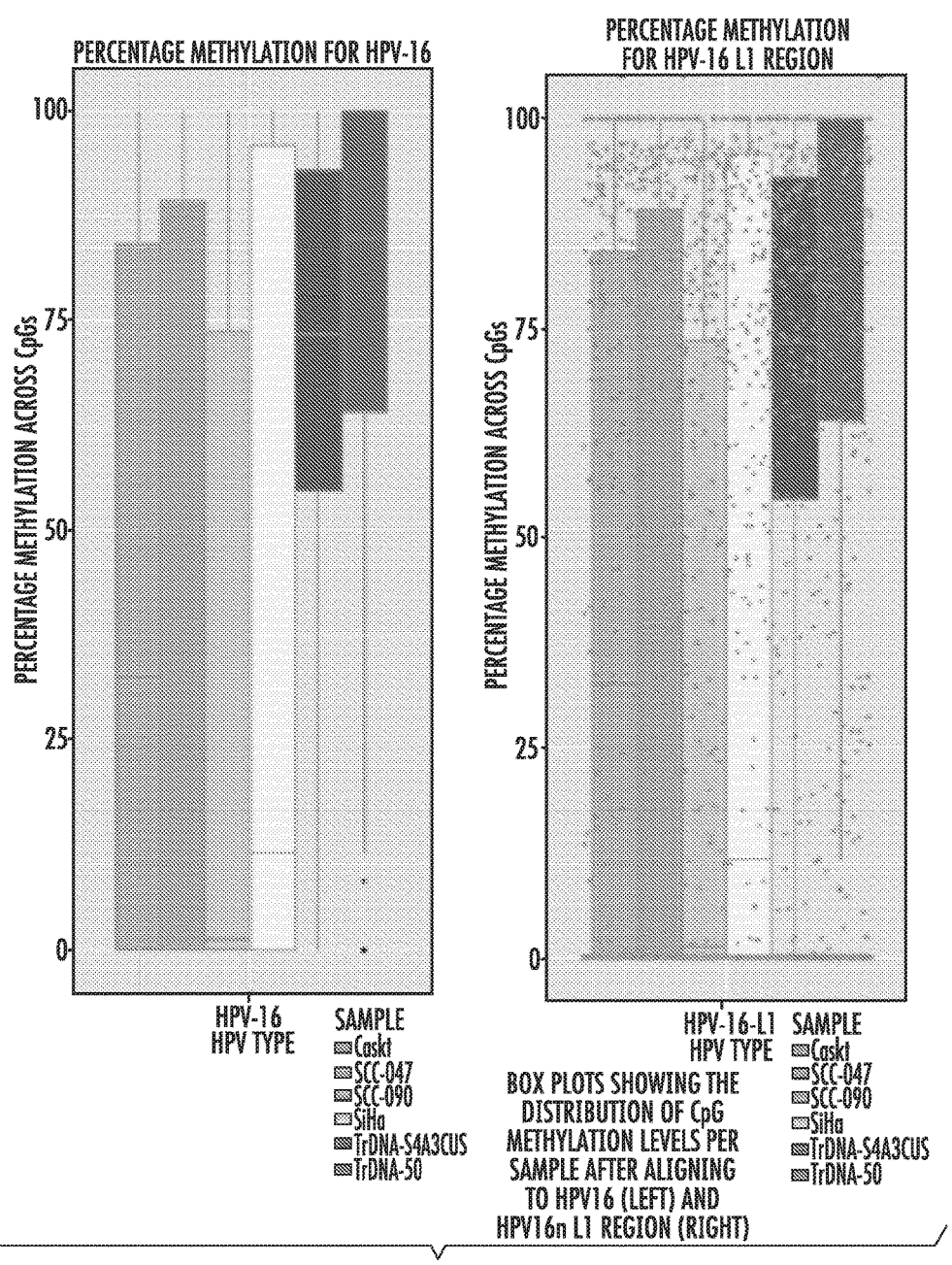
Figure 12:
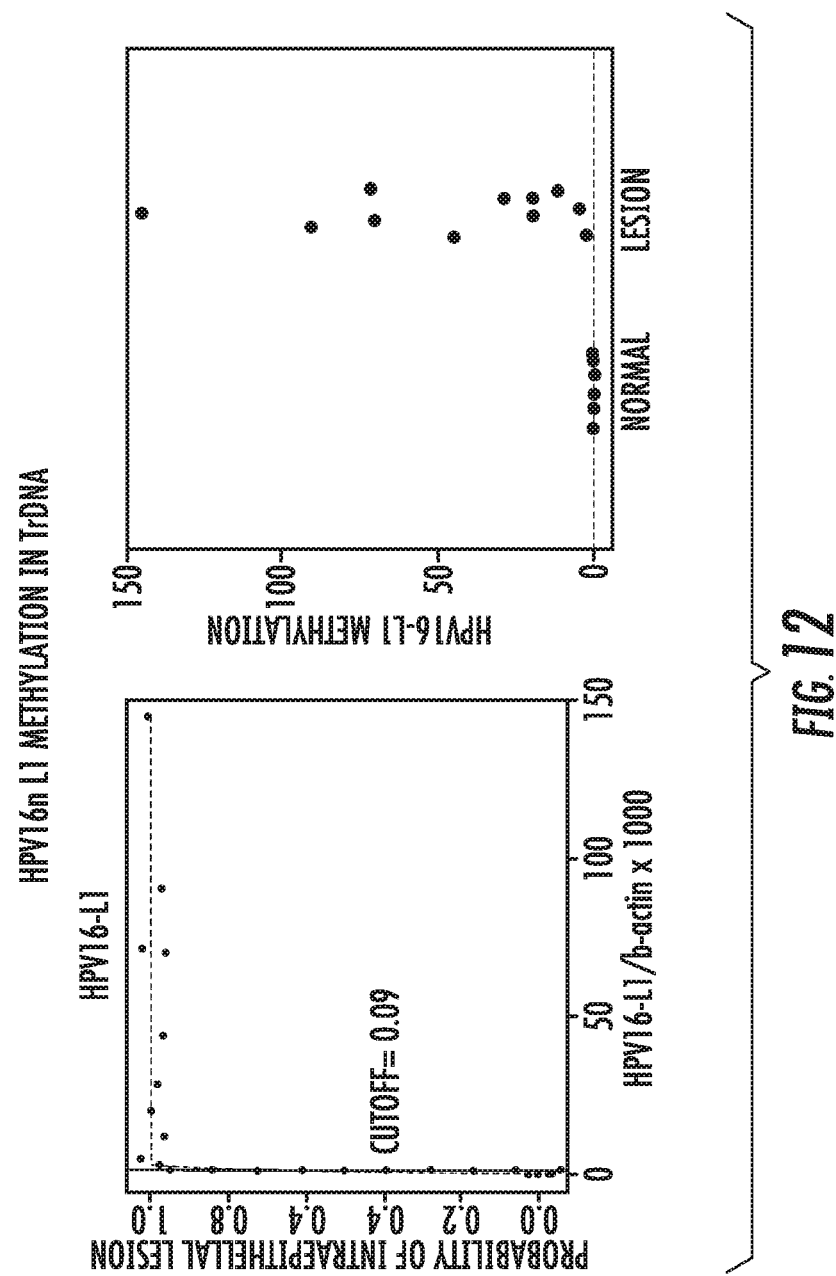
Figure 13:
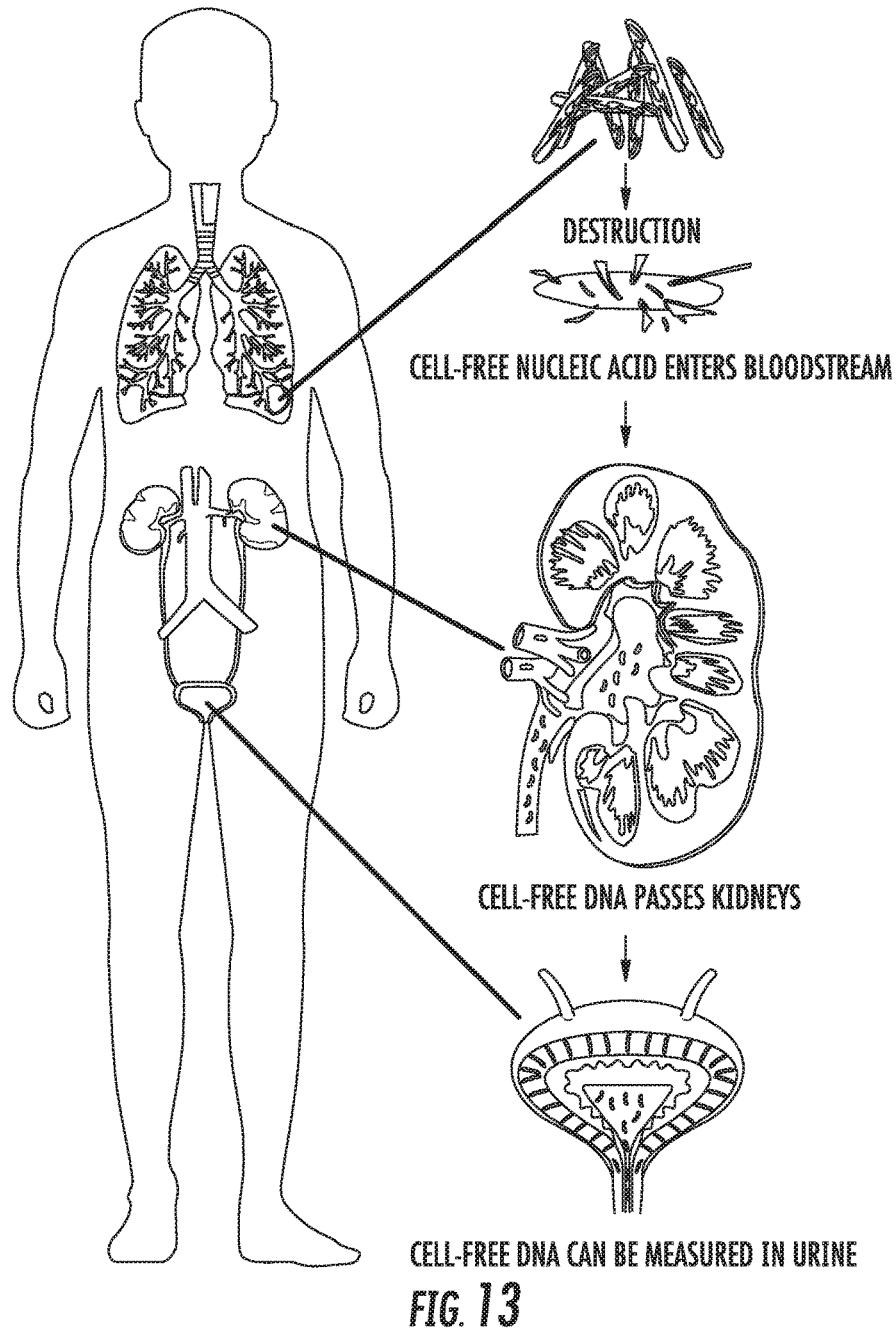
Figure 13:
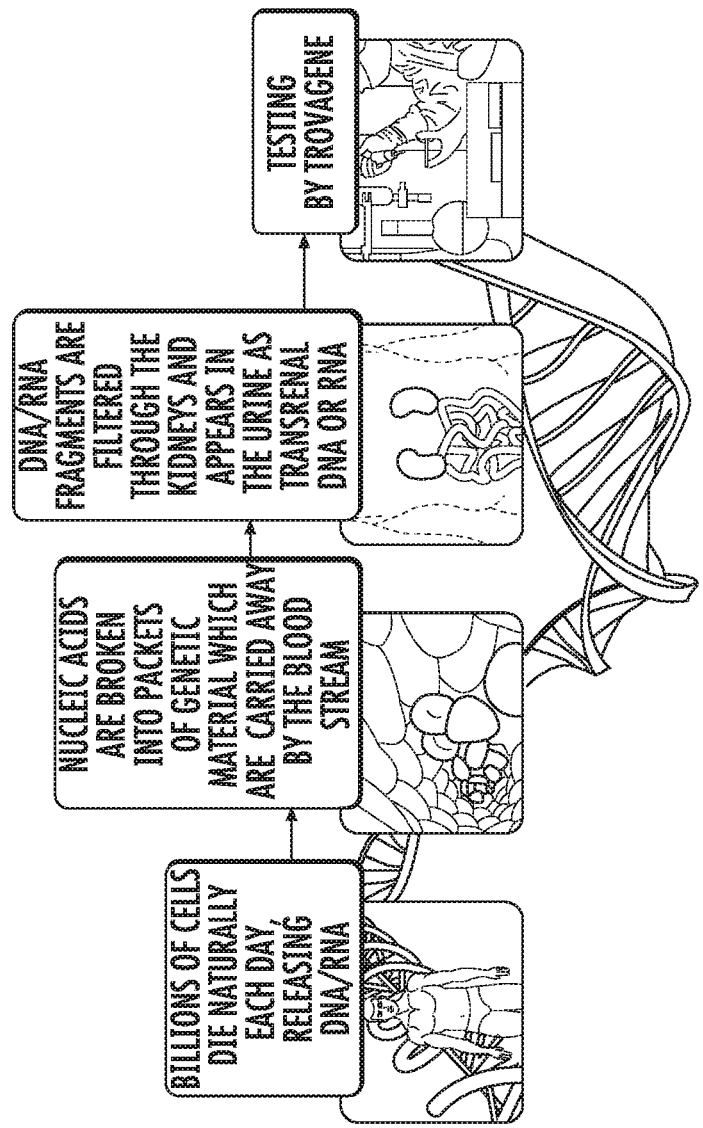
Figure 14:
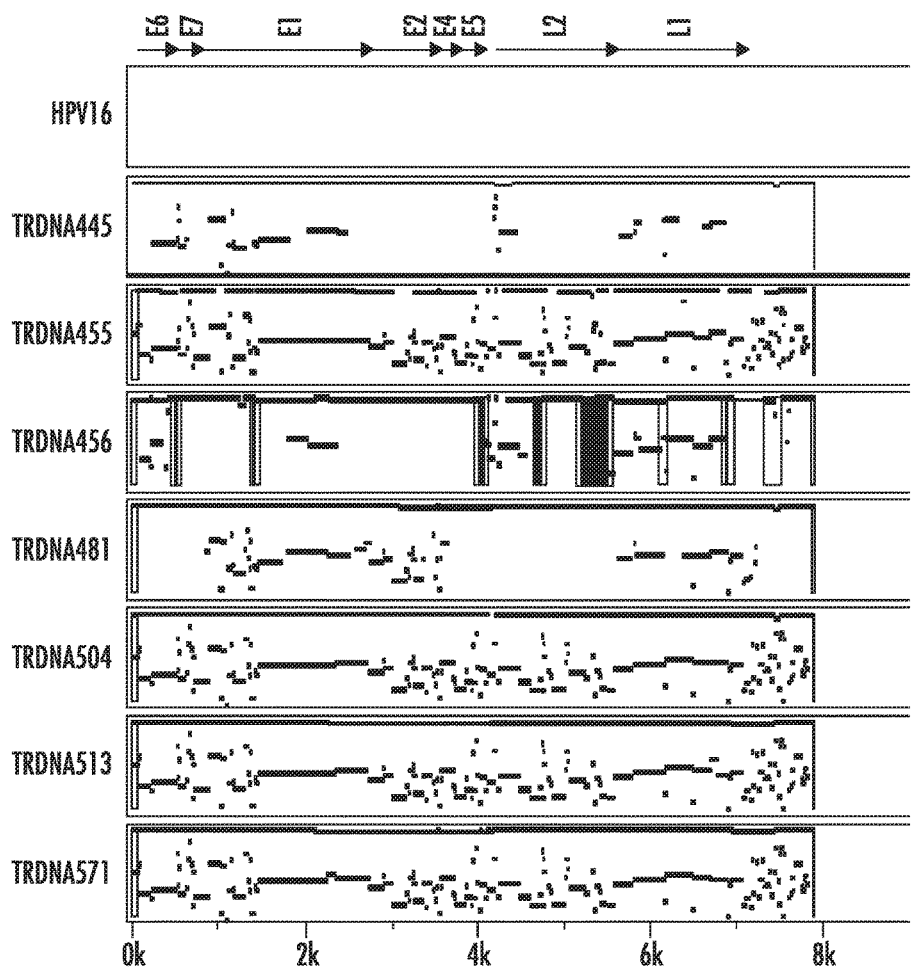

FIG. 6A shows ROC curves for HPV16-L1 methylation and ZNF516, FKBP6 and INTS1 promoter methylation in plasma ccfDNA samples from patients diagnosed with CIN2+ and NILM, with area under ROC curve=0.8075. FIG. 6B shows ROC curves for HPV16-L1 methylation and ZNF516, FKBP6 and INTS1 promoter methylation in urine ccfDNA samples from patients diagnosed with CIN2+ and NILM, with area under ROC curve=0.8611;

FIG. 7 shows a custom-designed pool of HPV-specific dual sequence capture probes was used for library amplification and target selection in ccfDNAs (Roche/NimbleGen SeqCap EZ Choice Library). Using a SYBR green qPCR assay, an HPV E1 region common to thirteen high-risk HPV types was amplified;

FIG. 8 shows an amplification plot demonstrating the successful HPV amplification and enrichment obtained with dual sequence capture. Delta Ct values for HeLa (pink/red) and CSCC7 (purples) were 14.88 and 12.66 respectively. Based on an estimated efficiency for the assay, the approximate fold enrichment was greater than 1700;

FIG. 9 shows Pre- and Post-Capture HPV qPCR results for five ccfDNA samples together with HeLa genomic control (dark blue) and no DNA controls (purple);

FIG. 10 shows a profiling of sample TrDNA-456 by tiered read mapping to various databases, the graph indicates the percentage of reads that map to thirteen (13) HPV types, human, bacteria and unknown genomes after profiling reads of the clinical sample TrDNA-456 by tiered read mapping;

FIG. 11 shows box plots showing the distribution of CpG methylation levels per sample after aligning to HPV16 (left) and HPV16-L1 region (right). The CpG methylation median in the clinical samples is significantly higher than in the cell lines and higher in urine ccfDNA from the CIN3 than from the CIN1 clinical sample (p<0.05), as expected;

FIG. 12 shows Scatter plots of HPV16-L1 methylation in urine ccfDNA. HPV16-L1 qMSP methylation can discriminate bisulfate treated urine ccfDNA from patients with normal cytology (n=10) from women with dysplastic cytology and premalignant cervical lesions (ASCUS n=8; CIN1 n=3; CIN2+ n=3) with 100% Sensitivity and Specificity;

FIG. 13 shows circulating cell-free Renal DNA (ccfDNA) isolation results in the table. The table shows the comparison between DNA concentration obtained by isolating DNA from urine from the same participants utilizing two different extraction methods: Phenol chloroform (PC) and ccfDNA isolation methods; the illustrations shows a schematic of one concept of how ccfDNA enters the blood and urine of the subject;

FIG. 14 shows a table comprising dual sequence capture of high risk HPV in ccfDNA aligned to all high risk HPV types and low risk HPV types from PaVE database (top) and box plots of dual sequence capture of high risk HPV in ccfDNA aligned to all high risk HPV types and low risk HPV types (bottom); and FIG. 15 shows pairwise alignment of the HPV16 genome with reads obtained from urine ccfDNA from seven clinical samples: TrDNA-445, TrDNA-455, TrDNA-456, TrDNA-481, TrDNA-504, TrDNA-513, and TrDNA-571. The "close-up" HPV DNA computes and displays nucleotide-level (close-up') multiple alignments of sequences in a 1 Kb region starting at a user-specified address or gene in the reference genome.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides methods and kits for triaging a human papillomavirus (HPV)-positive woman into colposcopy. It has been found that a group of genes exhibit increased promoter methylation in women having CIN2+ lesions as compared to women having no intraepithelial lesions or malignancy (NILM). The presently disclosed methods provide a triage test that can discriminate between those women with no intraepithelial lesions or malignancy (NILM) and women with abnormal cervical biopsies (CIN1, CIN2, CIN3), carcinoma in-situ, and cervical cancer.

Rapid advances in genomic technologies and TCGA have revealed extensive, previously unsuspected complexity in human cancers. This complexity has led to calls for "precision medicine" to address the underlying complex genetic and epigenetic processes that underlie somatic cell evolution to malignancy. The present inventive methods take a significant step forward to improve precision medicine based on DNA sequence changes in methylation and mutation of the somatic genome of the patient and HPV. The inventive methods are anchored in the phases of biomarker development as published by NCI EDRN several years ago. They also include cloud based approaches for generalized testing and implementation of early detection strategies. Specific strategies employed include DNA sequence based assays such as quantitative Methylation Specific PCR, bisulfate genomic sequencing, and Next Generation Sequencing, all of which generate complex datasets reflecting the complexity of neoplastic evolution in human tissues. The inventive methods also propose testing urine samples using methods that optimize DNA isolation to enrich for cell free fragmented DNA (cffDNA) that is excreted in the urine, which opens a novel approach to early detection. The cloud based tools proposed in the methods could eventually be used by patients, providers, researchers and even insurance personnel. This type of "precision medicine" approach based on the actual DNA methylation and DNA nucleotide changes in the evolving virus and neoplasm of necessity vastly increase the complexity of the data.

I. Methods for Triaging a Human Papillomavirus (HPV)-Positive Woman into Colposcopy In some embodiments, the presently disclosed subject matter provides a method for triaging a human papillomavirus (HPV)-positive woman into colposcopy, the method comprising: (a) selecting a HPV-positive woman testing positive for one or more high risk types of HPV; (b) obtaining nucleic acid from a test sample from the selected HPV-positive woman; (c) determining in the nucleic acid from the test sample of the selected HPV-positive woman a promoter methylation level of the promoter regions of a group of genes that exhibit increased promoter methylation in women having CIN2+ lesions as compared to women having no intraepithelial lesions or malignancy (NILM); and (d) triaging the HPV-positive woman into colposcopy when the level of promoter methylation of the group of genes is increased relative to the level of promoter methylation of the group of genes in a reference sample obtained from women having NILM.

As used herein, the term "colposcopy" refers to a medical procedure that uses a device, such as a magnifying device, to view the cervix of a woman. If a problem is seen during a colposcopy, a small tissue sample or biopsy can be taken from the cervix or from inside of the opening of the cervix. A goal of a colposcopy is to detect cervical dysplasia, such as intraepithelial lesions, premalignant cervical neoplasia lesions and/or cervical cancer lesions. As used herein, the term "triaging" refers to the sorting of and/or allocation of treatment to patients, particularly those women at risk for cervical cancer.

As used herein, a human papillomavirus (HPV)-positive woman or a woman who tests positive for HPV is a woman who has been infected with HPV, particularly a high risk type of HPV. The term "high-risk HPV" as used herein refers to those HPV types or strains that may progress to precancerous lesions and invasive cancer, such as cervical cancer. Non-limiting examples of high-risk HPV strains that are known or thought to cause cervical cancer include HPV 16, 18, 26, 31, 33, 35, 39, 45, 51, 52, 53, 56, 58, 59, 66, 68, 73, and 82. In some embodiments, one or more high risk types of HPV are selected from the group consisting of HPV16, HPV18, HPV31, HPV33, HPV35, HPV39, HPV45, HPV51, HPV52, HPV56, HPV58, HPV59, and HPV68. In some embodiments, a woman who has been infected with a high risk type of HPV is selected for triaging using the presently disclosed methods. In some embodiments, the HPV-positive woman is further selected on the basis of abnormal cytology, such as a woman who has cervical cells that do not appear normal in shape, size, and/or composition. In some embodiments, the abnormal cytology comprises low squamous intraepithelial lesions (LSIL). In some embodiments, the abnormal cytology comprises high squamous intraepithelial lesions (HSIL). In some embodiments, the HPV-positive woman does not have abnormal cytology of cervical cells. In some embodiments, abnormal cytology is tested for by using a Papanicolaou test (Pap-test). In some embodiments, the HPV-positive woman has had a negative, positive, or inconclusive Pap smear.

In some embodiments, selecting the HPV-positive woman testing positive for one or more high risk types of HPV comprises determining whether the nucleic acid is homologous to one or more high risk types of HPV. In some embodiments, determining whether the nucleic acid is homologous to one or more high risk types of HPV comprises performing at least one HPV detection assay selected from the group consisting of nucleic acid sequencing (e.g., Sanger sequencing, third generation sequencing, and the like), PCR, a HPV genotyping assay, a microarray assay, and a mRNA based assay. An example of a HPV detection assay is disclosed in PCT Patent Application No. PCT/US2014/019934, which is hereby incorporated by reference in its entirety. Methods to determine homology between two nucleic acid sequences are well known in the art and any method that can be used to determine homology can be used for the presently disclosed methods.

In some embodiments, determining whether the nucleic acid is homologous to one or more high risk types of HPV comprises: (a) sequencing the nucleic acid to produce a nucleotide sequence; (b) performing a sequence alignment between the nucleotide sequence and the nucleotide sequence of the one or more high risk types of HPV; and (c) determining the percentage sequence identity between the nucleotide sequence and the nucleotide sequence of the one or more high risk types of HPV.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences that differ by such conservative substitutions are said to have sequence similarity. Approaches for making this adjustment are well-known to those of skill in the art.

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Algorithmic programs for sequence comparisons and/or searching sequences against databases are well known in the art, such as FASTA, BLAST, SAHA, MUMmer, AVID, CHAOS, QUASAR, and the like.

The terms "substantial identity" or "homologous" in their various grammatical forms in the context of polynucleotides means that a polynucleotide comprises a sequence that has a desired identity, for example, at least about 60% or more identity, such as 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% or higher identity compared to a reference sequence. Alignment programs using standard parameters can be used to determine percent identity. In some embodiments, at least a 60% sequence identity between the nucleotide sequence from the test sample and the nucleotide sequence of the one or more high risk types of HPV means that at least one high risk HPV strain has been detected in the woman.

In some embodiments, nucleic acid is obtained from a test sample from the selected HPV-positive woman. Non-limiting examples of a test sample include a tissue specimen, a biopsy specimen, a surgical specimen, a cervical swab, a cytological specimen, a plasma specimen, a serum specimen, and a urine specimen. In some embodiments, the test sample from the woman is from a specimen selected from the group consisting of a tissue specimen, a biopsy specimen, a surgical specimen, a cervical swab, a cytological specimen, a plasma specimen and a urine specimen. In some embodiments, the test sample from the woman comprises a specimen selected from the group consisting of liquid prep, plasma, serum, and urine. As used herein, the term "liquid prep sample" refers to a sample that is in a fluid, such as a sample comprising cervical cells in a preservative liquid. Particularly, "liquid prep sample" can refer to a solution that comprises cervical cells that have been collected from a woman, such as by a tool (e.g., a brush, a self-collection swab, a tampon, and the like). In some embodiments, the test sample refers to the liquid prep sample where the Pap and HPV test were performed, otherwise known as a reflex test. In some embodiments, the test sample refers to a self-collected cervical cytology or urine sample. Test samples will desirably contain cervical cells when they are collected from the cervical mucosa and/or circulating DNA from cervical cells, when it is isolated from urine as ccfDNA.

As used herein, a "nucleic acid" or "polynucleotide" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

It may be beneficial to extract nucleic acids from the cells prior to testing. Some techniques of testing may not require pre-extraction. In some embodiments, as used herein, "obtaining" the nucleic acid from a test sample means using the nucleic acid in the test sample in an assay, such as a promoter methylation assay. In some embodiments, "obtaining" the nucleic acid means to separate the nucleic acid from other molecules found in the test sample, such as lipids, carbohydrates and proteins. Separating the nucleic acid may occur by any technique known in the art, for example, extraction with organic solvents, filtration, precipitation, absorption on solid matrices (e.g., silica resin, hydroxyapatite or ion exchange), affinity chromatography (e.g., via sequence specific capture or nucleic acid specific ligands), molecular exclusion chromatography, and the like. In some embodiments, the nucleic acid comprises DNA. In some embodiments, the nucleic acid comprises ccfDNA, which are relatively short, fragmented pieces of circulating DNA that get filtered by the kidneys and can be isolated from urine. In some embodiments, the nucleic acid is from about 150 to about 250 base pairs.

In some embodiments, after obtaining nucleic acid from the test sample from a woman, a promoter methylation level of the promoter regions of a group of genes is determined. It has been found that the promoter methylation level of the promoter regions of a group of genes exhibit increased promoter methylation in women having CIN2+ lesions as compared to women having no intraepithelial lesions or malignancy (NILM).

In some embodiments, the group of genes consists of, consists essentially of, or comprises a combination of at least three of the woman's endogenous genes. As used herein, the term "endogenous gene" of a woman is a gene that originated within the woman, as compared to a viral gene found in a sample taken from the woman, which did not originate within the woman. In some embodiments, the group of genes consists of, consists essentially of, or comprises ZNF516 (e.g., NCBI Gene ID 9658), FKBP6 (e.g., NCBI Gene ID 8468), and INTS1 (e.g., NCBI Gene ID 26173).

In some embodiments, the group of genes consists of, consists essentially of, or comprises a combination of at least one of the woman's endogenous genes and at least one HPV gene. In some embodiments, the combination of at least one of the woman's endogenous genes and at least one HPV gene consists of, consists essentially of, or comprises ZNF516, FKBP6, and INTS1 and HPV gene HPV16-L1.

Any tests can be used to detect promoter methylation. Suitable tests which can be used without limitation include lab-on-chip technology, microfluidic technologies, biomonitor technology, proton recognition technologies (e.g., Ion Torrent), single cell third generation sequencing (e.g. PacBio or Oxford Nanopore MinION hand-held sequencer; http://phys.org/news/2015-06-professors-handheld-dna-sequencer.html), and other highly parallel and/or deep sequencing methods. In some embodiments, determining the promoter methylation level comprises performing bisulfite modification to the nucleic acid from the test sample to produce a bisulfite modified nucleic acid. DNA methylation is a biochemical process whereby a methyl group is added to the cytosine or adenine DNA nucleotides. CG dinucleotides tend to cluster in regions called CpG islands, mainly present in the promoters of genes. Promoter methylation can directly switch off gene expression by preventing transcription factors binding to promoters.

Bisulfite compounds, for example, sodium bisulfite, convert non-methylated cytosine residues to bisulfite modified cytosine residues. The bisulfite ion treated gene sequence can be exposed to alkaline conditions, which convert bisulfite modified cytosine residues to uracil residues. Sodium bisulfite reacts readily with the 5,6-double bond of cytosine (but poorly with methylated cytosine) to form a sulfonated cytosine reaction intermediate that is susceptible to deamination, giving rise to a sulfonated uracil. The sulfonate group can be removed by exposure to alkaline conditions, resulting in the formation of uracil. The DNA can be amplified, for example, by PCR, and sequenced to determine whether CpG sites are methylated in the DNA of the sample. Uracil is recognized as a thymine by Taq polymerase and, upon PCR, the resultant product contains cytosine only at the position where 5-methylcytosine was present in the starting template DNA. One can compare the amount or distribution of uracil residues in the bisulfite ion treated gene sequence of the test cell with a similarly treated corresponding non-methylated gene sequence. A decrease in the amount or distribution of uracil residues in the gene from the test cell indicates methylation of cytosine residues in CpG dinucleotides in the gene of the test cell. The amount or distribution of uracil residues also can be detected by contacting the bisulfite ion treated target gene sequence, following exposure to alkaline conditions, with an oligonucleotide that selectively hybridizes to a nucleotide sequence of the target gene that either contains uracil residues or that lacks uracil residues, but not both, and detecting selective hybridization (or the absence thereof) of the oligonucleotide. Examples of performing bisulfite modification to a nucleic acid to determine hypermethylation of the nucleic acid are disclosed in U.S. Pat. No. 8,859,468, which is hereby incorporated by reference in its entirety. In some embodiments, the level of the bisulfite-modified nucleic acid is measured by sequencing of the bisulfite-modified nucleic acid.

In some embodiments, the level of the bisulfite modified nucleic acid is measured by quantitative real-time methylation specific PCR (QMSP). In general, PCR refers to an in vitro method for amplifying or replicating a specific polynucleotide template sequence. The PCR reaction involves a repetitive series of temperature cycles. The reaction mix usually comprises dNTPs (each of the four deoxynucleotides dATP, dCTP, dGTP, and dTTP), primers, buffers, DNA polymerase, and target nucleic acid molecule or template. The PCR step can use a variety of thermostable DNA-dependent DNA polymerases, such as Taq DNA polymerase, which has a 5'-3' nuclease activity but lacks a 3'-5' proofreading endonuclease activity. In real-time or quantitative PCR, the DNA is amplified and simultaneously quantified. QMSP protocols adopt the advantages of real-time PCR by using fluorescent-labeled MSP primers. Non-limiting examples of QMSP variations include Syber green-based QMSP, sensitive melting analysis after real-time MSP, and methylation-specific fluorescent amplicon generation.

In some embodiments, the quantitative real-time methylation specific PCR (QMSP) and/or sequencing of the bisulfite modified nucleic acid is performed using primers and/or probes specific for the group of genes. In some embodiments, a combination of the woman's endogenous genes consists of, consists essentially of, or comprises ZNF516, FKBP6, and INTS1 and HPV gene HPV16. In some embodiments, the primers and/or probes are selected from the group consisting of SEQ ID NOS: 1-12.

In some embodiments, the methylation status of the nucleic acid(s) of the one or more genes of interest are obtained by performing at least one human DNA methylation detection assay selected from the group consisting of nucleic acid sequencing, PCR, a microarray assay, a restriction enzyme selection assay, a sequence capture assay, or an affinity enrichment assay.

In some other embodiments, the methylation status of the nucleic acid is obtained by performing at least one HPV DNA methylation detection assay selected from the group consisting of nucleic acid sequencing, PCR, a microarray assay, a restriction enzyme selection assay, a sequence capture assay, or an affinity enrichment assay.

The terms "increased," "increase," "enhance," or "activate" are all used herein to generally mean an increase by a statically significant amount; for the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. A ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative. Diagnostic tests that use these biomarkers may show a ROC of at least about 0.6, at least about 0.7, at least about 0.8, or at least about 0.9.

The promoter methylation level is differentially present in women having CIN2+ lesions and women having no intra-epithelial lesions or malignancy (NILM), and therefore, is useful in triaging a HPV-positive woman into colposcopy. In certain aspects, the promoter methylation level of a group of genes is measured in a test sample using the methods described herein and compared, for example, to predefined promoter methylation levels and correlated to Cervical Intra-epithelial Neoplasia (CIN) grade. In particular aspects, the measurement(s) may then be compared with a relevant diagnostic amount(s), cut-off(s), or multivariate model scores that distinguish a NILM grade from a CIN2+ grade. The diagnostic amount(s) represents a measured amount of a promoter methylation level of a group of genes above which or below which a woman is classified as having a particular CIN grade. As is well understood in the art, by adjusting the particular diagnostic cut-off(s) used in an assay, one can increase the sensitivity or specificity of the diagnostic assay. In particular aspects, the diagnostic cut-off can be determined, for example, by measuring the amount of promoter methylation levels of a group of genes in a statistically significant number of samples from women with the different CIN grades, and drawing the cut-off to suit the desired levels of specificity and sensitivity.

In some embodiments, the presently disclosed method has a specificity of at least 60%. In some embodiments, the method has a sensitivity of at least 90%. In some embodiments, the method has a positive predictive value (PPV) of at least 52%. In some embodiments, the method has a negative predictive value (NPV) of at least 90%.

In some embodiments, the group of genes consists of, consists essentially of, or comprises ZNF516, FKBP6, and INTS1 and the specificity is at least 88%, the sensitivity is at least 88%, the positive predictive value (PPV) is at least 93%, and the negative predictive value (NPV) is at least 90%.

In some embodiments, the group of genes consists of, consists essentially of, or comprises ZNF516, FKBP6, and INTS1 and HPV gene HPV16-L1, and the specificity is at least 60%, the sensitivity is at least 90%, the positive predictive value (PPV) is at least 52%, and the negative predictive value (NPV) is at least 93%.

In some embodiments, the presently disclosed methods further comprise enriching the nucleic acid from the test sample before determining the promoter methylation level. In some embodiments, enriching the nucleic acid from the test sample comprises: (a) preparing a library of the nucleic acid from the test sample; (b) amplifying the library using PCR to form a pre-capture PCR library; (c) hybridizing the pre-capture PCR library to a custom-designed pool of HPV-specific and human-specific capture probes to form a post-capture PCR library; (d) amplifying the post-capture PCR library to produce enriched nucleic acid; and (e) optionally repeating steps (c) and (d).

The term "enriching" as used herein means to purify or partially purify the molecule of interest. In some embodiments, the custom-designed pool of HPV-specific and human-specific capture probes is designed to capture most or all of the genomes of high-risk HPV-specific types. In some embodiments, the custom-designed pool of HPV-specific and human-specific capture probes is designed to capture only some regions of the genotype-specific regions of at least one high-risk HPV genome, such as 1, 2, 3, 4, or 5 or more regions. In some embodiments, the custom-designed pool of HPV-specific and human-specific capture probes is designed to capture 2 to 3 regions of the HPV genome that distinguishes high-risk from low-risk HPV types. In some embodiments, the custom-designed pool of HPV-specific and human-specific capture probes does not capture low-risk HPV types. In some embodiments, the custom-designed pool of HPV-specific and human-specific capture probes is designed to capture regions of the HPV16 genome. In some embodiments, the custom-designed pool of HPV-specific and human-specific capture probes is designed to capture most or all of the genomes of the group of genes that exhibit increased promoter methylation in women having CIN2+ lesions as compared to women having no intra-epithelial lesions or malignancy (NILM). In some embodiments, the custom-designed pool of HPV-specific and human-specific capture probes is designed to capture most or all of the promoters of the group of genes that exhibit increased promoter methylation in women having CIN2+ lesions as compared to women having no intraepithelial lesions or malignancy (NILM). In some embodiments, the custom-designed pool of HPV-specific and human-specific capture probes is designed to capture most or all of the promoters of ZNF516, FKBP6, and INTS1.

In some embodiments, the presently disclosed subject matter provides a method for triaging a human papillomavirus (HPV)-positive woman into colposcopy, the method comprising: (a) selecting a HPV-positive woman testing positive for one or more high risk types of HPV; (b) providing a kit that comprises the probes and/or primers needed for determining in the nucleic acid from a test sample of the selected HPV-positive woman a promoter methylation level of the promoter regions of a group of genes that exhibit increased promoter methylation in women having CIN2+ lesions as compared to women having no intraepithelial lesions or malignancy (NILM); (c) obtaining nucleic acid from the test sample from the selected HPV-positive woman; (d) determining the promoter methylation level in the nucleic acid from the test sample of the selected HPV-positive woman using the provided kit; and (e) triaging the HPV-positive woman into colposcopy when the level of promoter methylation of the group of genes is increased relative to the level of promoter methylation of the group of genes in a reference sample obtained from women having NILM. In some embodiments, the kit comprises the probes and/or primers needed for determining in the nucleic acid from the test sample of the selected HPV-positive woman the promoter methylation level of the promoter regions of the group of genes consisting of, consisting essentially of, or comprising ZNF516, FKBP6, and INTS1 and HPV gene HPV16-L1.

In some embodiments, the presently disclosed subject matter further comprises informing the woman or a treating physician of the result of the method of triaging the human papillomavirus (HPV)-positive woman into colposcopy. In some embodiments, the presently disclosed methods further comprise performing a colposcopy. In some embodiments, the presently disclosed subject matter further comprises providing a prognosis regarding the development of cervical cancer based on the colposcopy performed. In some embodiments, for example if the presently disclosed methods are negative for promoter methylation, the methods further comprise recommending that the woman continue to be screened or retested at regular intervals, such as every six months, every year, every two years, every three years or more.

In some embodiments, the presently disclosed subject matter further comprises diagnosing the woman as having cervical pre-cancerous lesions and/or cervical cancer.

In some embodiments, the presently disclosed subject matter further comprises recommending treatment and/or treating the woman. Treatment may include removal of precancerous lesions; radiation treatment; surgery, such as a hysterectomy, removal of lymph nodes, a cone biopsy, and/or a trachelectomy; and/or chemotherapy, using for example a platinum-containing anti-cancer drug (e.g. cisplatin) and/or a topisomerase inhibitor (e.g., topotecan). In some embodiments, the treatment is selected from the group consisting of removal of precancerous lesions, radiation treatment, surgery, and chemotherapy.

In some embodiments, the presently disclosed methods further comprise monitoring the efficacy of the treatment. Monitoring may occur by performing a Pap smear, performing a colposcopy, testing for the presence of a high risk type of HPV, and/or using the presently disclosed methods. In some embodiments, monitoring the efficacy of the treatment occurs by at least one method selected from the group consisting of performing a Pap smear, performing a colposcopy, testing for the presence of a high risk type of HPV, and determining a promoter methylation level of the promoter regions of a group of genes that exhibit increased promoter methylation in women having CIN2+ lesions as compared to women having no intraepithelial lesions or malignancy (NILM).

II. Kits for Triaging a Human Papillomavirus (HPV)-Positive Woman into Colposcopy The presently disclosed subject matter also relates to kits for practicing the methods of the invention. By "kit" is intended any article of manufacture (e.g., a package or a container) comprising primers and/or probes specific for a group of genes that exhibit increased promoter methylation in women having CIN2+ lesions as compared to women having no intraepithelial lesions or malignancy (NILM).

In some embodiments, the presently disclosed subject matter provides a kit for triaging a human papillomavirus (HPV)-positive woman into colposcopy, the kit comprising: (a) a container containing primers and/or probes specific for a group of genes that exhibit increased promoter methylation in women having CIN2+ lesions as compared to women having no intraepithelial lesions or malignancy (NILM); and (b) instructions for use of the primers and/or probes in triaging a human papillomavirus (HPV)-positive woman into colposcopy.

In some embodiments, the group of genes consists of, consists essentially of, or comprises ZNF516, FKBP6, and INTS1. In some embodiments, the group of genes consists of, consists essentially of, or comprises ZNF516, FKBP6, and INTS1 and HPV gene HPV16. In some embodiments, the primers and/or probes are selected from the group consisting of SEQ ID NOS: 1-12.

III. Methods for Treating Cervical Cancer

In some embodiments, the presently disclosed subject matter provides methods for treating cervical cancer. In some embodiments, the presently disclosed subject matter provides a method for treating cervical cancer, the method comprising: (a) selecting a HPV-positive woman testing positive for one or more high risk types of HPV; (b)

providing a kit that comprises the probes and/or primers needed for determining in the nucleic acid from a test sample of the selected HPV-positive woman a promoter methylation level of the promoter regions of a group of genes that exhibit increased promoter methylation in women having CIN2+ lesions as compared to women having no intraepithelial lesions or malignancy (NILM); (c) obtaining nucleic acid from the test sample from the selected HPV-positive woman; (d) determining the promoter methylation level in the nucleic acid from the test sample of the selected HPV-positive woman using the provided kit; (e) triaging the HPV-positive woman into colposcopy when the level of promoter methylation of the group of genes is increased relative to the level of promoter methylation of the group of genes in a reference sample obtained from women having NILM; (f) performing a colposcopy; (g) diagnosing the woman as having cervical pre-cancerous lesions and/or cervical cancer; and (h) treating the woman for cervical cancer. Optionally, the presently disclosed methods include providing a prognosis regarding the development of cervical cancer based on the colposcopy performed.

Treatment of the woman for cervical cancer may include removal of precancerous lesions; radiation treatment; surgery, such as a hysterectomy, removal of lymph nodes, a cone biopsy, and/or a trachelectomy; and/or chemotherapy. Non-limiting therapeutic agents that can be used in the treatment of the woman for cervical cancer include platinum-containing anti-cancer drug (e.g., cisplatin, carboplatin), topisomerase inhibitors (e.g., topotecan), tubulin targeting agents (e.g., paclitaxel), pyrimidine analogs (e.g, fluorouracil), nucleoside analogs (e.g., gemcitabine), anti-mitotic agents (e.g., docetaxel), and alkylating agents (e.g., cyclophosphamide).

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Human Papilloma Virus (HPV) testing is increasingly used for cervical cancer screening in conjunction with cervical cytology. Although privacy, cultural, and infrastructure issues challenge the effective implementation of HPV testing for cervical cancer screening worldwide, several countries have already implemented HPV testing in their screening protocols. There are currently no tests that can reliably identify the patients with abnormal cytology and positive oncogenic HPV results (HPV+) that need to be referred for colposcopy. A triage test from cytology to colposcopy needs to be able to discriminate in the cytology sample those patients with a Cervical Intraepithelial Neoplasia (CIN) grade more likely to progress to cervical cancer (CIN2+).

We set out to identify a panel of methylated human papilloma virus (HPV) and human genes that can discriminate between CIN2+ and normal/CIN1 patients in liquid prep samples and transrenal DNA isolated from urine (ccfDNA).

Methods: We used three independent cohorts, from Chile, Baltimore, and Puerto Rico, to develop a method that can be used to triage into colposcopy, HPV+ women with abnormal cytology. Participants were women with no cervical intraepithelial lesions or malignancy, and women with: abnormal cervical biopsies (CIN1, CIN2, CIN3); carcinoma in-situ, and cervical cancer.

Using DNA methylation arrays for Discovery and quantitative Methylation Specific PCR (qMSP) for Validation, we found that promoter methylation of ZNF516, FKBP6, and INTS1 discriminates samples with CIN2+ lesions from samples with no intraepithelial lesions or malignancy (NILM): 88.3% sensitivity, 88.9% specificity, 93.2 Area Under the Curve (AUC), 86.9% positive predictive value (PPV) and 90.2% negative predictive value (NPV). Using custom sequence capture pools of baits, we pulled down genomic and bisulfate converted high-risk HPV DNA before library prep for NGS in 454 and MiSeq instruments, respectively. Using our NGS results, we optimized a Syber Greeen qPCR assay to detect high risk HPV DNA and a qMSP primer-probe set to detect methylated HPV. We replicated the results in liquid prep samples (n=67), adding HPV16 methylation to the panel: 90.9% sensitivity, 60.9% specificity, 90.1 (AUC), 52.6% positive predictive value (PPV) and 93.3% NPV. These results were verified in plasma DNA (AUC=80.7) and ccfDNA (AUC=86.1) isolated from a subset of patients who provided the liquid prep samples.

Our results suggest that our panel of viral and host gene methylation markers may be used as a reflex test in liquid prep to triage high risk HPV positive women into colposcopy, or as a screening and triage test in ccfDNA, in combination with our high risk HPV test. The presently disclosed methods can be used to triage into colposcopy, women with abnormal Pap smears and positive oncogenic HPV results (HPV+) using host and viral DNA methylation markers in liquid prep and ccfDNA.

Results

DNA samples isolated from cervical brush (n=211), liquid cytology (n=107), serum (n=40) and ccfDNA (n=130) from women with normal cervical epithelium, premalignant cervical neoplasia lesions and cervical cancer lesions were examined to test the performance of viral and host DNA methylation markers as classifiers for triage into colposcopy (FIGS. 1a-b). We first identified a panel of host DNA methylation markers associated with CIN2+ biopsy lesions using genome-wide DNA methylation arrays for Discovery and qMSP for Validation in cervical brush samples from Chile. This classifier was previously associated with cervical cancer and abnormal cytology samples in the same cohort (23).

Cervical brush samples (n=211) were genotyped for HPV with the Reverse Line Blot assay. After removing samples without a definitive biopsy result, we examined the promoter methylation frequency of three genes (ZNF516, INTS1 and FKBP6) in cervical brush samples from women with normal (n=34), CIN1 (n=34), CIN2 (n=33) and CIN3 (n=20) and cervical cancer (n=90) pathology reports. We compared samples from women with no intraepithelial lesions or malignancy (NILM) and CIN1 lesions with samples from women with CIN2+ lesions, and found that: ZNF516 has 91.7% Sensitivity, 27.4% Specificity and an AUC of 0.62; FKBP6 has 92.4% Sensitivity, 46.8% Specificity and an AUC of 0.68; INTS1 has 93.8% Sensitivity, 30.3% Specificity and an AUC of 0.57. We then compared samples from women with NILM to samples from women with CIN2+ lesions, we found that: ZNF516 has 91.7% Sensitivity, 38.9% Specificity and an AUC of 0.76; FKBP6 has 90.9% Sensitivity, 67.6% Specificity and an AUC of 0.86; INTS1 has 90.7% Sensitivity, 40.5% Specificity and an AUC of 0.62.

The panel of three classifiers (ZNF516, INTS1 and FKBP6) has 90% Sensitivity, 88.9% Specificity, an AUC of 0.93, a Positive Predictive Value (PPV) of 93.1% and a Negative Predictive Value (NPV) of 84.2%, when comparing women with no intraepithelial lesions or malignancy (NILM) with women with CIN2+ lesions (Table 1 below, FIGS. 2a and 2b).

TABLE 1

Table 1. Promoter methylation frequency in cervical brush samples Chile - cytobrush n = 211

| Lesion comparison | Marker | Sensitivity % | Specificity % | AUC % | PPV % | NPV % |
|---|---|---|---|---|---|---|
| CIN2+ vs. NILM/CIN1 | ZNF516 | 91.7 | 27.4 | 61.6 | | |
| | FKBP6 | 92.4 | 46.8 | 68.4 | | |
| | INTS1 | 93.8 | 30.3 | 56.9 | | |
| | 3 gene panel | 60 | 74.5 | 77 | 57.1 | 76.7 |
| CIN2+ vs. NILM | ZNF516 | 91.7 | 38.9 | 76.5 | | |
| | FKBP6 | 90.9 | 67.6 | 85.6 | | |
| | INTS1 | 90.7 | 40.5 | 62.2 | | |
| | 3 gene panel | 88.3 | 88.9 | 93.2 | 86.9 | 90.2 |

We then tested this panel of three classifiers in liquid-based cytology samples (n=67) from women in Puerto Rico, a subset of which had been previously tested for concordance of high risk HPV genotype between liquid prep and urine DNA (30). We compared samples from women with NILM and CIN1 lesions with samples from women with CIN2+ lesions and found that: ZNF516 has 72.7% Sensitivity, 48.1% Specificity and an AUC of 0.63; FKBP6 has 63.6% Sensitivity, 34.6% Specificity and an AUC of 0.50; INTS1 has 91% Sensitivity, 35% Specificity and an AUC of 0.66. We also tested the performance of HPV16-L1 methylation, using previously designed primers and probes (39), and found it had 63.6% Sensitivity, 57.7% Specificity and an AUC of 0.54. Then we compared samples from women with NILM with samples from women with CIN2+ lesions, we found that: ZNF516 has 63.6% Sensitivity, 17.4% Specificity and an AUC of 0.50; FKBP6 has 63.6% Sensitivity, 39.1% Specificity and an AUC of 0.50; INTS1 has 63.6% Sensitivity, 39.1% Specificity and an AUC of 0.47. We also tested the performance of HPV16-L1 methylation and found it had 63.6% Sensitivity, 100% Specificity and an AUC of 0.79.

The panel of four classifiers in liquid prep samples, ZNF516, INTS1, FKBP6 and HPV16-L1 has 90.9% Sensitivity, 60.9% Specificity, an AUC of 0.90, a PPV of 52.6% and a NPV of 93.3% when comparing NILM with CIN2+ lesions (Table 2 below, FIGS. 3A and 3B).

TABLE 2

Table 2. Promoter methylation frequency in liquid prep samples UPR - Liquid prep n = 67

| Lesion comparison | Marker | Sensitivity % | Specificity % | AUC % | PPV % | NPV % |
|---|---|---|---|---|---|---|
| CIN2+ vs. NILM/CIN1 | ZNF516 | 72.7 | 48.1 | 63.5 | | |
| | FKBP6 | 63.6 | 34.6 | 49.8 | | |
| | INTS1 | 90.9 | 34.6 | 66.1 | | |
| | HPV16-L1 | 63.6 | 57.7 | 54.2 | | |
| | 4 gene panel | 90.9 | 46.15 | 73.1 | 26.3 | 96 |
| CIN2+ vs. NILM | ZNF516 | 63.6 | 17.4 | 50 | | |
| | FKBP6 | 63.6 | 39.1 | 50.1 | | |
| | INTS1 | 63.6 | 39.1 | 46.6 | | |
| | HPV16-L1 | 63.6 | 100 | 78.7 | | |
| | 4 gene panel | 90.9 | 60.9 | 90.1 | 52.6 | 93.3 |

Example 2

Sequencing the hrHPV Genome in Urine ccfDNA

To enable the testing of this four gene panel in ccfDNA, we optimized a previously published ccfDNA isolation method and compared it to the gold standard, phenol chloroform DNA extraction method (FIG. 13). We developed sequence capture methods and quantitative PCR assays to measure HPV high-risk types and methylated HPV CpGs in ccfDNA from women with and without cervical dysplasia.

To examine the hrHPV genome in urine ccfDNA we developed custom dual-sequence capture baits (FIG. 7), to enrich samples for hrHPV DNA from 12 high-risk types (HPV 16, 18, 31, 33, 35, 39, 45, 51, 52, 56, 58, and 59). To assess the enrichment efficiency of the dual sequence capture method we developed the hrHPV ccfDNA-qPCR assay with primers that amplify the HPV E1 region common to 13 high-risk HPV types (HPV 16, 18, 31, 33, 35, 39, 45, 51, 52, 56, 58, 59 and 68). We compared pre-capture and post-capture DNA from cervical cancer cell lines that harbor high risk HPV, HeLa (HPV18) and CSCC7 (HPV16). PicoGreen quantitation was performed on both pre-capture and post-capture DNA samples, and a normalized amount of DNA (5 ng) was analyzed. FIG. 8 shows an amplification plot demonstrating the successful amplification and enrichment obtained with the dual sequence capture assay. Delta Ct values for HeLa and CSCC7 were 14.88 and 12.66, respectively. Based on an estimated efficiency for the assay, approximate fold enrichment was greater than 1700.

To assess the enrichment efficiency of the dual sequence capture method on clinical samples, we compared the HPV ccfDNA-qPCR assay results obtained on eight (8) pre-capture and post-capture HPV-enriched circulating DNA samples obtained from patients with CIN1 (n=4) and CIN2-3 (n=4). As shown in FIG. 9, with data representing five clinical samples, the average Delta Ct value for Pre-Capture vs. Post-Capture HPV-enriched ccfDNAs was 11.07, for an average fold enrichment of 670 of HPV ccfDNA in patient samples.

We then examined if the HPV ccfDNA-qPCR assay could discriminate ccfDNA isolated from women with and without cervical dysplasia. FIG. 4 shows the amplification curves for the HPV ccfDNA-qPCR assay on ccfDNA from CIN2-3 (n=14), CIN1 (n=13) and 10 samples from women with NILM. The frequency of dysplastic samples that amplified differed significantly from NILM samples, but not with lesion severity: NILM (30%), CIN1 (77%, p=0.02), and CIN2+ (71%, p=0.04).

We then used massively parallel next generation sequencing to quantify the different HPV genotypes present in ccfDNA from 7 patients with CIN1 (n=3) and CIN2-3 (n=4), using DNA from two cervical cancer cell lines (HeLa and CSCC7) as positive controls. The DNA was enriched for high risk HPV DNA with the custom dual sequence capture high risk HPV assay prior to multiplexed sequencing on a 454 GS Junior (Roche) system. The multiplexed massively parallel sequencing runs produced 230,385 reads with an average length of 138.3 bp. The reads in the clinical samples covered 82-100% of the reference HPV 16 and 73-100% of the HPV 18 genomes, with an average of 21% (HPV18) to 33% (HPV18) percentage of all reads mapping to the sequences. These results were comparable to the percentage of all reads that mapped to the reference sequences in the positive control samples: 92% of the CSCC7 reads mapped on target covering 77% of the HPV16 genome; and 89% of the HeLa reads mapped to 67% of HPV 18, as expected (Table 3).

TABLE 3

Table 3. Dual sequence capture of high risk HPV in TrDNA
Dual Sequence capture of high risk HPV in TrDNA
aligned to HPV 16 and HPV 18

| | | | | | HPV16ref | | | HPV18ref | | |
|---|---|---|---|---|---|---|---|---|---|---|
| Sample ID | Lesion | HPV | Input DNA (ng) | # Reads | unique match reads | % of all reads | % coverage | unique match reads | % of all reads | % coverage |
| HeLa | cancer | 18 | 250 | 51952 | cell line with hpv18 | | | 46284 | 89.1 | 67.07 |
| CSCC7 | cancer | 16 | 250 | 48095 | 44262 | 92 | 76.6 | cell line with hpv16 | | |
| TrDNA445 | CIN3 | 16.45 | 60 | 25998 | 24670 | 95 | 100 | 772 | 3 | 73.4 |
| TrDNA455 | CIN1 | 18 | 100 | 55002 | 144 | 0.3 | 81.6 | 53075 | 96.5 | 100 |
| TrDNA456 | CIN1 | 33 | 100 | 45982 | 953 | 2.1 | 91.4 | 1647 | 3.6 | 74.3 |
| TrDNA481 | CIN3 | 16 | 55 | 18159 | 6700 | 37 | 100 | 1185 | 6.5 | 87.1 |
| TrDNA504 | CIN3 | 16 | 60 | 33218 | 11227 | 33.8 | 99.4 | 4624 | 13.9 | 100 |
| TrDNA513 | CIN1 | 16.66 | 30 | 25242 | 5085 | 20.1 | 100 | 2202 | 8.7 | 100 |
| TrDNA571 | CIN3 | 16 | 100 | 26472 | 12229 | 46 | 100 | 3989 | 15.1 | 100 |
| Average | | | 72 | 32868 | 8715 | 33 | 96 | 9635 | 21 | 91 |

To quantify the presence and HPV genotype composition of the patient samples, we first aligned the reads against the >170 human HPV genomes in the PapillomaVirus Episteme (PaVE) database, maintained by the NIH NIAID Samples TrDNA_445 and TrDNA_455 had more than 80% of their reads mapped to HPV 16 and HPV 18, however, the remaining five samples were somewhat split, mapping to both HPV 16 and 18 genotypes, with many not mapping to either (FIG. 14 and Table 4 below).

TABLE 4

Profiling of HPV TrDNA 454 reads by tiered mapping

| READS | Human papillomavirus type |
|---|---|
| 193 | Human papillomavirus type 44, complete genome |
| 24 | Human papillomavirus type 61, complete genome |
| 841 | Human papillomavirus type 56 clone Qv24970, complete genome |
| 243 | Human papillomavirus type 45 isolate Qv31035, complete genome |
| 231 | Human papillomavirus type 72 |
| 109 | Human papillomavirus type 11 isolate LZod45-11; complete genome |
| 837 | Human papillomavirus type 42 isolate TJ43-42, complete genome |
| 54 | Human papillomavirus type 53 isolate TJ43-53, complete genome |
| 493 | Human papillomavirus type 18 complete sequence |
| 732 | Human papillomavirus type 16, complete genome |
| 421 | Human papillomavirus type 68b, complete genome |
| 226 | Human papillomavirus type 6 complete genome, isolate CAC231 |
| 156 | Human papillomavirus 39 |

TABLE 4-continued

Profiling of HPV TrDNA 454 reads by tiered mapping

| READS | Human papillomavirus type |
|---|---|
| 330 | Human papillomavirus type 31 isolate QV12357, complete genome |
| 10060 | Human papillomavirus type 33 isolate Qv34189, complete genome |
| 564 | Human papillomavirus type 35 isolate QV29782, complete genome |
| 145 | Human papillomavirus type 52 isolate Qv-03594, complete genome |
| 1533 | Human papillomavirus type 58 isolate Z094, complete genome |
| 184 | Human papillomavirus type 81 complete genome |
| 17645 | Human papilloma virus type 59, complete viral genome |
| 48 | Human papillomavirus 54, complete genome |
| 10913 | Unmapped |

To resolve the remaining reads, we searched the human genome using the program Bowtie (39), and then a local copy of the database of NCBI reference bacterial genomes, using BLAST (40). Following this tiered mapping approach, only a small number of reads were still mapping to unknown genomes, a small number of which (<50) were linker contaminants, while the others could potentially represent novel HPV genotypes or other viruses or bacteria (FIG. 14 and Table 4 above, representing sample TrDNA_456). FIGS. 4, 8 and 9 show the percentage of reads that align to different HPV types, human, bacteria and unknown genomes for this same sample, TrDNA_456. Table 4 lists the reads mapping to twenty-one (21) HPV types after profiling reads of the clinical sample TrDNA-456 by tiered read mapping. FIG. 10 shows the percentage of reads that map to thirteen (13) HPV types, human, bacteria and unknown genomes for clinical sample TrDNA-456.

Cloud-Based Visualization Tools of the HPV Genome for Personalized Medicine

We used two Cloud-based tools, which allow the comparative visualization of HPV genomes uploaded by users against a reference genome of interest (43). Our demonstration cloud-based servers show the alignment results of 11 hrHPV types, 9 low risk HPV types, and seven clinical samples (TrDNA-445, TrDNA-455, TrDNA-456, TrDNA-481, TrDNA-504, TrDNA-513, and TrDNA-571) against a reference genome (HPV16).

The large-scale HPV DNA server (http://enterix.cbcb.umd.edu/enteric/enteric-hpv.html) produces a graphical 'large-scale' view of the pairwise alignments of twenty HPV genomes against a reference genome (HPV16 in this demo), together with annotations of genome rearrangement events (FIG. 14 top).

The "close-up" HPV DNA server (http://enterix.cbcb.umd.edu/menteric/enteric-hpv.html) computes and displays nucleotide-level (close-up') multiple alignments of sequences in a 1 Kb region starting at a user-specified address or gene in the reference genome (FIG. 14 bottom).

Sequencing the hrHPV Epigenome in Urine ccfDNA

To examine the hrHPV genome in urine ccfDNA we used the Sure Select Methyl-Seq Target Enrichment (Agilent) assay to enrich DNA samples from two HPV16 positive cervical cancer cell lines, CaSki (ATCC® CRL-1550™, 600 integrated HPV16 copies) and SiHa (ATCC® HTB35™, 2 integrated HPV16 copies); two HPV16 positive Head and Neck Squamous Cell Carcinoma cell lines, SCC-47 and SCC-90; and urine ccfDNA from two clinical samples: one from a patient with ASCUS and CIN1 (TrDNA47) and another one from a patient with HSIL and CIN3 (TrDNA50). Samples were PCR-amplified using sample-specific indexed ("barcoding") primers for multiplexed sequencing on a MiSeq (Illumina) system.

Reads from the FASTQ files were aligned to all HPV types in the PAVE database and we performed CpG methylation analysis using Bismark, modified to analyze high-risk HPV genomes. The multiplexed massively parallel sequencing run produced 14,442,406 reads with a length of 100 bp. The percentage of all reads of the HPV positive cervical cancer and head and neck cancer squamous cell carcinoma (HNSCC) cell lines that mapped uniquely to some of the reference genomes in the PAVE database can be seen in the top panel of (Table 5 below) Caski (93%); SiHa (13%); SCC-047 (68%) and SCC-090 (87%).

TABLE 5

Alignment of HPV genotype from the custom sequence capture method against the PapillomaVirus Episteme (PaVE) database

| Sample | Reference_genome | Total_Reads | Reads_No_Alignment | Reads_Aligned_uniquely | Mapping_efficiency |
|---|---|---|---|---|---|
| Caski | HPV_pave_all | 1648170 | 119552 | 1528618 | 93% |
| SiHa | HPV_pave_all | 1838822 | 1597909 | 240913 | 13% |
| SCC-047 | HPV_pave_all | 2391854 | 759528 | 1632326 | 68% |
| SCC-090 | HPV_pave_all | 2806373 | 363874 | 2442499 | 87% |
| TrDNA-34(CIN1) | HPV_pave_all | 3183371 | 3181520 | 1848 | 0% |
| TrDNA-50(CIN3) | HPV_pave_all | 2573816 | 2568941 | 4869 | 0% |
| Total | | 14442406 | 8591324 | 5851073 | |
| Average | | 2407068 | 1431887 | 975179 | 44% |
| Caski | HPV-16 | | 142622 | 1505548 | 91% |
| SiHa | HPV-16 | | 1602013 | 236809 | 13% |
| SCC-047 | HPV-16 | | 814051 | 1577803 | 66% |
| SCC-090 | HPV-16 | | 397578 | 2406795 | 86% |
| TrDNA-34(CIN1) | HPV-16 | | 3181642 | 1729 | >1% |
| TrDNA-50(CIN3) | HPV-16 | | 2572738 | 1078 | >1% |
| Total | | | 8712644 | 5729762 | |
| Average | | | 1452107 | 954960 | 43% |
| Caski | HPV_16_11 | | 1356064 | 292106 | 18% |
| SiHa | HPV_16_11 | | 1791950 | 46872 | 3% |
| SCC-047 | HPV_16_11 | | 2043910 | 347944 | 15% |

TABLE 5-continued

Alignment of HPV genotype from the custom sequence capture method against the PapillomaVirus Episteme (PaVE) database

| Sample | Reference_genome | Total_Reads | Reads_No_Alignment | Reads_Aligned_uniquely | Mapping_efficiency |
|---|---|---|---|---|---|
| SCC-090 | HPV_16_11 | | 2375812 | 430561 | 15% |
| TrDNA-34(CIN1) | HPV_16_11 | | 3182952 | 419 | >1% |
| TrDNA-50(CIN3) | HPV_16_11 | | 2573606 | 210 | >1% |
| Total | | | 13324294 | 1118112 | |
| Average | | | 2220716 | 186352 | 9% |

Towards Personalized HPV Methylation Landscapes

The percentage of methylation across the HPV genome in all six samples was obtained with the Methylator Extractor module in Bismark. Scatterplots of the percentage of methylation by chromosomal location in the HPV genome for each of the six samples are show in FIG. 4. The percentage of methylation is shown on the Y-axis of the upper panel. The X-axis shows the chromosomal location along the HPV genome for both panels, including the promoters at positions 97 and 670 of the HPV genome. The upper panel of each plot represents the percentage of CpG methylation. The bottom panel of each plot represents the HPV genes and the Upper Regulatory Region (41).

The different HPV genomes that aligned to the six samples are shown in different colors and shapes (HPV16-black dots; HPV35 red squares; HPV52 red triangles; and HPV71 green squares). The two cervical cancer cell lines had different patterns of CpG methylation. Caski had overall higher levels of methylation than SiHA for CpGs across the genome. SiHA exhibits a bimodal distribution of methylation percentage. The majority of CpGs below the 3500 position in the HPV genome have less than 60% methylation, while CpGs located between 3500 and 7200 positions on the HPV genome show over 80% methylation. This may be related to the low number of HPV copies per genome present in this cell line. The methylation patterns for both HPV positive HNSCC cell lines were very similar to those observed in Caski. The clinical samples aligned to more than one HPV type. TrDNA-34, a sample obtained from a patient with ASCUS and CIN1, aligned to HPV16 and HPV35. TrDNA-50, a sample obtained from a patient with HSIL and CIN3, aligned to HPV16, HPV52 and HPV71. The methylation patterns of HPV16 in both clinical samples are very similar to the methylation patterns observed in Caski and both HNSCC cell lines, albeit with less abundant number of reads, as expected. Methylation of the remainder of HPV types was low overall.

To examine the HPV16 CpG methylation patterns we aligned the reads from the four cell lines to the HPV16 reference genome. The mapping efficiency (the percentage of total reads that aligned uniquely to the reference genome) to the HPV16 reference genome was very similar to the percentage of all reads that mapped to the PAVE reference database for the four cell lines: Caski (91%); SiHa (13%); SCC-047 (66%), and SCC-090 (86%). The mapping efficiency of the reads from the HNSCC cell lines to the HPV16 reference genome was in the range between the mapping efficiency obtained with SiHA and Caski, namely 86% for SCC-90 and 66% for SCC-47 (Table 5, middle panel). Since we know the number of copies of HPV16 DNA in SiHa (2) and Caski (~600), these sequencing results may be a good indicator of the number of HPV copies present in the HNSCC cell lines.

The clinical samples aligned to more than one HPV type. TrDNA-34, a sample obtained from a patient with ASCUS and CIN1, aligned to HPV16 and HPV35. TrDNA-50, a sample obtained from a patient with HSIL and CIN3, aligned to HPV16, HPV52 and HPV71. The methylation patterns of HPV16 in both clinical samples are very similar to the methylation patterns observed in Caski and both HNSCC cell lines, albeit with less abundant number of reads, as expected. Methylation of the remainder of HPV types was low overall.

Given that HPV type is defined by a measure of sequence divergence in the HPV L1 region of the genome, we divided the reads from the four cell lines that mapped only to the HPV16 L1 gene by the reads of the four cell lines that mapped to the HPV16 genome, to calculate their mapping efficiency to the HPV16-L1 gene. The mapping efficiency of the four cell lines to the HPV-16 L1 gene was high: Caski (81%); SiHA (80%); SCC-47 (78%) and SCC-90 (82%). Surprisingly, the mapping efficiency of the clinical samples to the HPV16 L1 gene was as high as for the positive controls: 76% for TrDNA-34 and 81% for TrDNA-50 (Table 6).

TABLE 6

Mapping efficiency to HPVL1

| Samples | Mapping_Efficiency to_HPVL1 |
|---|---|
| Caski | 81% |
| SCC-047 | 78% |
| SCC-090 | 82% |
| SiHa | 80% |
| TrDNA-34 | 76% |
| TrDNA-50 | 81% |

We wanted to assess whether methylation levels in the HPV16-L1 variable region could be used as a marker of progression in cervical cancer premalignant lesions. To determine whether the L1 region is uniformly represented in the reads, we calculated the ratio of the reads from each of the four cell lines that mapped only to the HPV16 L1 gene (Table 5, bottom panel) to the total number of reads from each cell line that mapped to the HPV16 genome, and determined the mapping efficiency to the HPV16-L1 gene. The mapping efficiency of the four cell lines to the HPV-16 L1 gene was high: Caski (81%); SiHA (80%); SCC-47 (78%) and SCC-90 (82%). The mapping efficiency of the clinical samples to the HPV16 L1 gene was as high as for the positive controls: 76% for TrDNA34 and 81% for TrDNA50 (FIG. 11).

To further determine if HPV16-L1 methylation levels can be used as a surrogate marker of methylation of the HPV16 genome in urine ccfDNA, we examined the distribution of CpG methylation after aligning the urine ccfDNA samples to the HPV16-L1 gene. The CpG methylation median in the clinical samples is significantly higher than in the cell lines and higher in urine ccfDNA from the CIN3 than from the CIN1 clinical sample (p<0.05), as expected (FIG. 11).

Quantification of Viral and Host DNA Methylation in Plasma and Urine ccfDNA

To enable the testing of this four-gene panel in urine ccfDNA, we optimized a previously published urine ccfDNA isolation method and compared it to the gold standard, phenol chloroform DNA extraction method (FIG. 13, Top). We then designed primers and Taqman probes to quantify HPV16 L1 DNA methylation and ZNF516, INTS1 and FKBP6 methylation in fragmented urine ccfDNA using qMSP. The genomic region of the HPV16 L1 gene used to design the Primers were designed to amplify in urine ccfDNA short amplicons (80 base-pairs long) of the same genomic regions previously used to quantify HPV16-L1 methylation in HNSCC (39); and ZNF516, INTS1 and FKBP6 in cervical cancer (18), In a feasibility study we found that HPV16-L1 qMSP methylation can discriminate bisulfite treated urine ccfDNA from patients with normal cytology (n=10) from women with dysplastic cytology and premalignant cervical lesions (ASCUS n=8; CIN1 n=3; CIN2+ n=3) with 100% sensitivity and specificity (FIG. 12).

We then quantified the methylation levels of the panel of viral and host DNA genes in plasma and urine ccfDNA samples from women with NILM and CIN2+ lesions. In plasma, we found the panel of four classifiers has 85.7% Sensitivity, 60.9% Specificity, an AUC of 0.807, PPV of 40% and a NPV of 93.3% (FIG. 6a). In urine ccfDNA, we found the panel of four classifiers has 75% Sensitivity, 83.3% Specificity, an AUC of 0.861, PPV of 50% and a NPV of 93.8% (FIG. 6b).

Discussion

The present inventors set out to identify a panel of methylated HPV and human host genes that can discriminate between CIN2+ and normal/CIN1 lesions in a reflex test performed in liquid prep samples and ccfDNA in plasma and urine. The inventors are the first to show that a panel of host and viral DNA methylation markers can discriminate between CIN2+ and NILM in multiple body compartments from the same individual: liquid prep, serum and urine. The results show that a precision medicine panel can be used as a reflex test in liquid prep to triage women referred to colposcopy. NGS reads from urine ccfDNA can be aligned in custom cloud-based servers for life-course personalized cervical cancer screening.

Women with low probability of having a CIN2+ lesion can be triaged out of a biopsy after colposcopy. The four-gene classifier best performed in liquid-prep with Sensitivity (90.9%), Specificity of 60.9% and NPV (93.3%). In urine ccfDNA, the four-gene classifier had equal NPV (93.8%), a better Specificity (83.3%) and similar AUC (0.861). The results obtained for this classifier in liquid prep and urine ccfDNA warrant further study of this panel as a molecular biomarker to triage women referred to colposcopy after testing positive for high-risk HPV and being diagnosed with cervical dysplasia with cytology. Women with low methylation values in this panel would be asked to return for follow-up cytology and HPV co-testing in 6-12 months, if the colposcopists do not see a clear indication of a lesion that should be biopsied. This would decrease the number of blind biopsies that are currently being performed, decreasing screening costs and increasing health care quality.

The inventors have developed a method that can be used to triage women with HPV+ abnormal Pap smears who have been referred to colposcopy. Participants were women living in Chile and Puerto Rico with no cervical intraepithelial lesions or malignancy and women with abnormal cervical biopsies-CIN2+. The inventors used methylation arrays during the Discovery phase, followed by bisulfite sequencing and quantitative Methylation Specific PCR (qMSP) during the Validation phase. Using custom sequence capture pools of baits, the inventors pulled down genomic and bisulfite converted high-risk HPV DNA before library prep for Next Generation Sequencing (NGS) in 454 and MiSeq instruments, respectively. Using the methylation arrays results, they optimized a Syber Greeen qPCR assay to detect high risk HPV DNA and a qMSP primer-probe set to quantify promoter methylation of ZNF516, FKBP6, and INTS1 in the host and the L1 gene in the HPV genome, in liquid prep and circulating cell free DNA (ccfDNA) in plasma and urine.

Additionally, we have quantified the circulating HPV methylome in urine, using a custom sequence capture approach, which allows for multiplexed massively parallel sequence of clinical sample, followed by qMSP verification. Our results also show that qMSP quantification of HPV16-L1 methylation is a surrogate of genome-wide HPV16 methylation, which could lead to high-throughput testing of HPV16-L1 methylation by qMSP, digital PCR or multiplexed massively parallel sequencing. Furthermore, the HPV16-L1 methylation assay discriminates ccfDNA in urine from women with cervical dysplasia when compared to women that do not have cervical dysplasia.

Cervical cancer affects more than 1,000,000 women worldwide. Around 470,000 new cases of cervical cancer are detected annually, mostly in developing nations, among which approximately half will die (42). Persistent mucosal infection with an oncogenic (high risk) HPV genotype is the most significant cause of cervical dysplasia and carcinoma (43). Only 14 of the genotypes are considered pathogenic or high-risk (44). Multiple studies have linked genotypes 16, 18, 31, 33, 35, 39, 45, 51, 52, 56, 58, 59, 66, and 68 to disease progression (45). Patients with a persistent infection with one of these types have an increased risk for developing severe dysplasia or cervical carcinoma (46).

Co-testing with cytology and HPV at 5-year intervals is now the preferred or acceptable strategy for cervical cancer screening for women aged 30-64 years in the US. Clinical management for HPV-positive/Pap-negative women, however, is not firmly established. In addition, there is increased resistance from the medical community to accept HPV-PAP co-testing for cervical cancer, due to the complex risk patterns associated to positive, negative, and undetermined cytology with positive and negative HPV results.

Clinical detection of HPV is typically performed by in-vitro diagnostic assays that detect viral genomic DNA, specifically the L1 gene, on mucosa samples collected by cervical scraping. However, because HPV infections are very common and because most women will clear HPV infections within 6 to 12 months, the presence of HPV DNA does not mean that cervical dysplasia or cervical cancer is present or that the infection will persist and the patient will progress to cervical cancer (13). Furthermore, cervical cancer screening programs currently in use are inefficient at identifying individuals at risk for disease, requiring multiple visits over a women's lifetime, which is costly and cumbersome (47). New methods for cervical cancer screening are needed to provide accurate, efficient and cost-effective ways of identifying women at risk for cervical cancer.

Methods

Patient Samples

Cervical brush, liquid-based cytology, serum/plasma and urine samples were obtained from collaborators Chile and Puerto Rico, under the Johns Hopkins University School of Medicine Institutional Review Board (IRB) approved protocol #NA 00020633. The IRB of the Doctor Hernán Henríquez Aravena (HHA) tertiary care regional hospital, in Temuco, Chile and IRB of the University of Puerto Rico School of Medicine also approved this protocol.

Sample Collection and Processing

Retrospective Cohort

DNA was isolated from the cervical epithelium and biopsy samples, genotyped for HPV with the Reverse Line Blot assay in Chile and sent to Johns Hopkins School of Medicine for epigenome-wide studies, as previously described (Epigenetics, 9, 308 (Feb. 1, 2014)).

Prospective Cohort

Samples were collected, flash frozen and sent to Johns Hopkins School of Medicine for DNA extraction with phenol/chloroform method, bisulfite conversion NGS, qPCR and qMSP analyses as described below.

Nucleic Acid Extraction

Cervical cytobrush, liquid-based cytology, and plasma/serum samples (n=40) were centrifuged and their pellets were digested with 1% SDS and 20 µg/mL proteinase K (Sigma) at 48° C. for 48 h, followed by phenol/chloroform extraction and ethanol precipitation.

Identification of Methylation Biomarkers of CIN2+ in Liquid-Based Cytology

We used quantitative Methylation Specific PCR (qMSP) to examine the association between CIN2+ biopsies and methylation of three genes (ZNF516, FKBP6, and INTS1) in cervical brush epithelium from a retrospective cohort, in which these genes are associated with cervical cancer and abnormal cytology (18). We verified the association between CIN2+ biopsies and methylation of ZNF516, FKBP6, INTS1 and HPV16-L1 in liquid-based cytology samples obtained from an independent prospective cohort.

Quantitative Methylation-Specific PCR (qMSP)

The methylation status of ZNF516, FKBP6, INTS1 and HPV16-L1 in bisulfite modified DNA from liquid-based cytology samples, plasma/serum and urine, was quantified with fluorescence-based quantitative methylation-specific PCR (qMSP) as described previously (Oncology Reports 32, 505 (August, 2014), Epigenetics, 9, (May 1, 2014)). Briefly, bisulfite converted DNA was used as template for fluorescence-based real-time PCR. Bisulfite sequencing (BS) was performed to determine the methylation status of the normal and tumor tissues prior to MSP. Bisulfite-treated DNA was amplified using BS primer sets for a 5' region within 800 bp of the TSS that included at least part of a CpG Island. The primer sequences did not contain CpG dinucleotides in order to obtain unbiased sequencing PCR products. Each amplified DNA sample was sequenced using forward or reverse primers. After verifying with bisulfite sequencing that we had located a suitable area in the promoter region for qMSP validation, MSP primers and qMSP probes were designed to specifically amplify this region in the candidate gene promoters. Primers and probes were tested on positive (in vitro methylated bisulfite converted DNA) and negative controls (genomic unmethylated bisulfite converted DNA) to ensure amplification of the desired product and non-amplification of unmethylated DNA, respectively. Primer and probe sequences are provided below.

Fluorogenic PCR reactions were performed in duplicates in a reaction volume of 20 µL that contained 3 µL of bisulfite-modified DNA; 600 nM concentrations of forward and reverse primers; 200 nM probe; 0.6 U of platinum Taq polymerase (Invitrogen, Frederick, Md.); 200 µM concentrations each of dATP, dCTP, dGTP and dTTP; and 6.7 mM MgCl2. Amplifications were performed using the reaction profile: 95° C. for 3 min, followed by 50 cycles at 95° C. for 15 s and 60° C. for 1 min in a 7900HT sequence detector (Applied Biosystems) and were analyzed by a sequence detector system software (SDS 2.4; Applied Biosystems).

Primers and Probes

Primers and probes sequences for the HPV16-L1 gene region and for the ccfDNA amplicons isolated from ccfDNA are shown below.

```
HPV16-L1
F:
                                           (SEQ ID NO: 1)
TATAGCGGTTGGTTTGGGTTTGTG

R:
                                           (SEQ ID NO: 2)
ACATTCTCTATTATCCACACCTACA

Probe:
                                           (SEQ ID NO: 3)
/56-FAM/AGGTGTTGAGGTAGGTCGTGG-TAMRA-Sp
``` ccfDNA Primers and Probes
(Probes are: 5'/56-FAM/-/ZEN/-/3IABkFQ/3')

```
FKBP6
F:
                                           (SEQ ID NO: 4)
ATATTTCGTATTTTATCGCG

R:
                                           (SEQ ID NO: 5)
ATCGTTTCGTTCCAACCG

Probe:
                                           (SEQ ID NO: 6)
CGACCCTAACCCTCGCGAACTCTA ZNF516
F:
                                           (SEQ ID NO: 7)
ACGGTGAGGTATGTATACG

R:
                                           (SEQ ID NO: 8)
ACTCGAAACCCTCAAAACG

Probe:
                                           (SEQ ID NO: 9)
AACGCCAAACCTCACCGTCGTACG INTS1
F:
                                           (SEQ ID NO: 10)
CGTTTTTCGTCGTCGTTTTA R:
                                           (SEQ ID NO: 11)
AAACAAAAAAATAACCGACGAT Probe:
                                           (SEQ ID NO: 12)
TATAACCTCCGCCCTCCCTCCCTA
```

Urine ccfDNA Extraction and Assessment

We adsorbed cell-free nucleic acids, on a Q-Sepharose anion-exchange resin followed by a silica-based elution with LiCl, from urine samples (10 mL) provided by 31 women with normal cervical cytology and 65 women with abnormal cervical cytology and biopsy: CIN1 (n=43) and CIN2-3

(n=22). ccfDNA samples were quantitated using the Quant-iT PicoGreen dsDNA reagent kit (Invitrogen, Life Technologies) and QuantiFluor ST spectrofluorometer (Promega). Concentrations were calculated based on readings obtained from Lambda DNA standards. Quality (fragment size) assessment of the ccfDNA samples was performed by High Sensitivity DNA Lab Chip analysis on a BioAnalyzer 2100 (Agilent). The urine ccfDNA samples selected for further processing showed size profiles in the 50-300 bp range, and exhibited low molecular weight DNA content.

ccfDNA hrHPV SYBR® Green Real-Time PCR

Validation of successful capture was assessed by the ccfDNA hrHPV qPCR assay on an Applied Biosystems Systems Prism 7500 Sequence Detection System. We designed SYBR® green quantitative PCR amplification assays of Beta-actin and the HPV E1 region that was used for the ccfDNA hrHPV capillary electrophoresis test (J. Clin. Microbiol. 52, 187 (January, 2014), J. Clin. Virol. (May 2, 2014)). This HPV E1 region is common to 13 high-risk HPV types (HPV 16, 18, 31, 33, 35, 39, 45, 51, 52, 56, 58, 59 and 68). The resulting amplicon is 93 bp. Beta-actin (β-actin), a housekeeping gene, was used as an indicator for successful extraction of an equivalent length of viral DNA targets. Serial dilutions of DNA isolated from cervical carcinoma cell line CaSki (ATCC® CRL-1550™, 600 integrated HPV16 copies) were run in parallel as positive controls. Primers were obtained from Invitrogen (Carlsbad, Calif.).

Custom Dual Sequence Capture Assay

HPV-specific, biotinylated, long oligonucleotide probes were designed, synthesized, and pooled for target selection and enrichment utilizing a dual capture approach (Roche/NimbleGen SeqCap EZ Choice Library). Probes were designed to capture the complete HPV genome and well-characterized variants representing 12 clinically relevant high-risk HPV types that have been associated with cervical cancer (HPV types 16, 18, 31, 33, 35, 39, 45, 52, 56, 58, 59 and 68b). The dual capture approach features two sequential captures of HPV target regions, with the output of the first capture amplified and used as targets for a second capture. The goal of this dual capture approach was a boost in both enrichment and specificity of HPV targets for deep sequencing.

Library preparation was performed using reagents in the GS FLX Titanium Rapid Library Preparation kit (Roche). To benchmark the assay we first worked with HPV positive cell lines: HeLa (HPV 18) and CSCC7 (HPV16). For these cell line samples, 250 ng genomic DNA was fragmented by nebulization, prior to ligation of double stranded, Rapid Library Multiplex Identifier (RL MID) adaptors, which added unique 10 base pair sequence tags to each library enabling multiplexing for sequencing, according to standard Roche protocol.

Methods in the Roche Rapid Library preparation manual were adapted to work with the fragmented ccfDNA obtained from urine and optimized to prepare libraries with as little as 30 nanograms of DNA (range=30-100 nanograms). Briefly, End-Polishing and A-tailing of fragments was performed, followed by ligation of the RL MID adaptors. Subsequently, two rounds of purification to remove un-ligated adaptors and adaptor dimers were performed on the fragments using AmPure XP beads according to standard Agencourt protocol. Quantitation of the library versus a FAM-labeled standard was performed using a QuantiFluor ST spectrofluorometer (Promega). Quality assessment of the Library was performed by High Sensitivity DNA Lab Chip analysis on a BioAnalyzer 2100 (Agilent). A pre-capture amplification of the library was performed with ligation-mediated PCR (LM-PCR) for 12 cycles using primers complementary to the adaptors, followed by two rounds of hybridization to the HPV-specific SeqCap EZ Choice Library. Each hybridization included enhancer oligonucleotides as well as Cot-1 Blocking DNA. After each hybridization step, a Streptavidin-coated, magnetic bead-based cleanup was performed, and the captured DNA was re-amplified by LM-PCR (5 cycles Post-Cap1, 15 cycles Post-Cap2). Subsequent to both Post-Cap LM-PCRs, purification was performed using the QiaQuick PCR purification kit (Qiagen). After Post-Cap2 LM-PCR, HPV-enriched ccfDNAs were quantitated by PicoGreen fluorescent assay and quality was assessed by DNA High Sensitivity Lab Chip analysis on the BioAnalyzer 2100.

A calculation of fold-enrichment was based on Ct values of captured vs. non-captured LM-PCR products in comparison with positive and negative controls. The amplified, HPV-enriched cell line DNAs and ccfDNAs were then diluted to a normalized concentration of 1×E08 molecules per microliter, pooled and processed for multiplexed sequencing on the GS Junior system (Roche).

Validation of successful capture was assessed by a XEN-HPV qPCR Sybr green assay on an Applied Biosystems Systems 7500 Sequence Detection System. A calculation of fold-enrichment was based on Ct values of captured vs. non-captured LM-PCR products in comparison with positive and negative controls. The amplified, HPV-enriched cell line DNAs and ccfDNAs were then diluted to a normalized concentration of 1×E08 molecules per microliter, pooled and processed for multiplexed sequencing on the GS Junior system (Roche).

RT-PCR Assay

A Perkin-Elmer/ABI 7900 thermocycler was used to run SYBR green quantitative PCR amplification assays for β-actin and the HPV E1 region that was used for the ccfDNA HPV capillary electrophoresis test. This ccfDNA HPV qPCR assay amplifies an HPV E1 region common to 13 high-risk HPV types (HPV 16, 18, 31, 33, 35, 39, 45, 51, 52, 56, 58, 59 and 68). The resulting amplicon is 93 bp. Primers were obtained from Invitrogen (Carlsbad, Calif.).

Sequencing on the GS Junior System

Processing for sequencing was according to Lib-L emPCR Amplification Method and Sequencing Method manuals, GS Titanium Series (Roche). A modification of reduced amplification primer (1:10 dilution) in the emPCR step was performed due to the small fragment size range. The DNA copy (fragment) to bead ratio for emPCR was 0.5. Sequence runs were performed on the GS Junior System.

Following completion of the sequencing runs, signal processing was performed, followed by QC analyses. Roche GS RunBrowser software deconvoluted the data, assigned each read to the appropriate library, and was used to assess QC metrics (% Keypass wells, % pass filtering, Average Read length, and Total bases). GS Reference Mapper, from the Roche GS Analysis Software Suite, was used for initial alignment to the HPV 16 and HPV 18 reference genomes. Detailed analysis was performed as described below.

Bioinformatics Analyses for GS Junior Output Reads.

To determine the HPV genotype composition of the patient samples, we searched the GS Junior 454 reads from each ccfDNA sample against the non-redundant database of HPV reference types compiled from the twelve high-risk and nine low-risk HPV reference genomes and the larger collection of PapillomaVirus Episteme (PAVE) genome database (48). Sequences were aligned to the reference genome database with the software sim4db (49), retaining only the best alignment covering 50% or more of the query sequence. To resolve the remaining reads, we first searched the human genome with the program bowtie (39), allowing for partial matches (option '--local'), and then the database of NCBI bacterial reference genomes, using the tool blast (40). Following this tiered mapping approach, only a small number of reads were still unclassified, of which a small number (<100) were linker contaminants, whereas the others could potentially represent novel HPV genotypes and other viruses or bacteria.

Custom Methylated HPV Sequence Capture and Sequencing

To quantify the HPV methylome by HPV type in ccfDNA we developed a methylated HPV sequence method (HPV ccfDNA Meth-seq) using custom designed baits (Table 5). The Sure Select Methyl-Seq Target Enrichment (Agilent) workflow, developed to capture the Human Methylome with a starting DNA amount of 3 µg, was optimized to capture the HPV methylome of 12 high-risk HPV types that have been associated with cervical cancer (HPV types 16, 18, 31, 33, 35, 39, 45, 52, 56, 58, 59 and 68b). Briefly, the Sure Select Methyl-Seq Library Prep Kit was used for End-Polishing and A-tailing of sheared DNA (150-200 bp) fragments, and subsequent ligation of methylated adaptors. These libraries were hybridized to target enrichment RNA baits in the custom SureSelect HPV Methyl-Seq bait library and hybrids were bound to streptavidin beads for enrichment. The target enriched gDNA library was then bisulfate treated and subsequently amplified by PCR and index tagged by a second PCR. The indexed, bisulfate-treated and enriched library was pooled, diluted to 2 nM, and submitted to the JHMI Synthesis and Sequencing Facility for sequencing on the Ilumina MiSeq system. The library was denatured using 0.2 N NaOH and diluted to a loading concentration of 15 pM. Sequencing was performed using a 2×150 MiSeq Reagent Kit v2 (300 cycle) with the run performed as a 2×100 paired-end run. The sample was loaded with a 5% PhiX control spike-in to account for the low diversity of the sample library. FASTQ files were generated and analyzed as follows.

Analysis of Sequencing Data

FASTQC version 0.11.3 was used for quality control of all the paired-end reads to assess per sequence base quality, per tile sequence quality, per sequence quality scores, per base sequence content, per sequence GC content, per base N content, sequence length distribution, sequence duplication levels, overrepresented sequences, adapter and kmer content. Reads were trimmed using Trim Galore v0.3.7. Default parameters were used, and one base pair was trimmed off at the end of all paired-end reads to improve paired-end mapping. If adapter contamination was observed, the standard Illumina adapters were trimmed off at the end of all paired-end reads. FASTQC post-trimming was rerun to perform quality control to ensure sure that the trimming step did not produce any adverse side effects.

Bioinformatics Analyses of Bisulfite-Converted Reads

Briefly, for alignment purposes Bismark converts all C's to T's (in forward reads) and all G's to A's (in reverse reads) prior to mapping and maps these in silico converted reads, to both a C-to-T and G-to-A in silico-converted genome. After successful alignment it replaces the T's and A's back to their original bases in all converted reads and compares it to the original reference genome to deduce methylated cytosines. Default parameters were used with the exception that "bowtie2 and 1 mismatch" was allowed during the alignment, retaining only the unique matches (default) and a seed length of 32. PCR duplicates were removed from the mapped reads using the "de-duplicate Bismark" routine. After running Bismark, post-alignment quality control was performed using Samtools version 0.1.19 and BamUtil version 1.0.12. Bismark divides all cytosines into four categories: cytosines followed by guanines (CpGs), cytosines followed by non-guanines followed by guanines (CHGs), cytosines followed by at least two non-guanines (CHHs), and cytosines followed by N's (CNs). Analysis for the current study focused on CpGs. The Default Bismark methylation extractor routine was used with the exception of --paired-end, --no-overlap, and minimum coverage of at least 1 read to extract all CpGs in individual samples.

Sequence similarity among HPV reference genomes could potentially impact the analysis, by disqualifying reads that map to several genomes. To eliminate or reduce these effects, we employed a two stage mapping procedure: i) we first aligned the reads against the entire genome database, using the unique matches to select those genotypes represented in the samples, and then ii) re-aligned the reads against the subset of genomes that were detected in that sample. Methylation maps for the HPV16 genome and restricted to the L1 region were produced with data produced by the Methylation Extractor from the Bismark suite.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

1. J. C. Gage et al., The low risk of precancer after a screening result of human papillomavirus-negative/atypical squamous cells of undetermined significance papanicolaou and implications for clinical management. *Cancer cytopathology*, (Jul. 9, 2014).
2. M. Schiffman et al., Human papillomavirus testing in the prevention of cervical cancer. *Journal of the National Cancer Institute* 103, 368 (Mar. 2, 2011).
3. G. Y. Ho, R. Bierman, L. Beardsley, C. J. Chang, R. D. Burk, Natural history of cervicovaginal papillomavirus infection in young women. *The New England journal of medicine* 338, 423 (Feb. 12, 1998).
4. M. R. McCredie et al., Natural history of cervical neoplasia and risk of invasive cancer in women with cervical intraepithelial neoplasia 3: a retrospective cohort study. *The lancet oncology* 9, 425 (May, 2008).

5. V. Cogliano et al., Carcinogenicity of human papillomaviruses. *The lancet oncology* 6, 204 (April, 2005).
6. P. E. Castle, J. C. Gage, C. M. Wheeler, M. Schiffman, The clinical meaning of a cervical intraepithelial neoplasia grade 1 biopsy. *Obstetrics and gynecology* 118, 1222 (December, 2011).
7. J. C. Gage et al., Comparison of the cobas Human Papillomavirus (HPV) test with the hybrid capture 2 and linear array HPV DNA tests. *Journal of clinical microbiology* 50, 61 (January, 2012).
8. D. Saslow et al., American Cancer Society, American Society for Colposcopy and Cervical Pathology, and American Society for Clinical Pathology screening guidelines for the prevention and early detection of cervical cancer. *American journal of clinical pathology* 137, 516 (April, 2012).
9. H. A. Katki et al., Five-year risks of CIN 3+ and cervical cancer among women who test Pap-negative but are HPV-positive. *Journal of lower genital tract disease* 17, S56 (April, 2013).
10. L. S. Massad et al., 2012 updated consensus guidelines for the management of abnormal cervical cancer screening tests and cancer precursors. *Obstetrics and gynecology* 121, 829 (April, 2013).
11. J. C. Gage et al., Reassurance against future risk of precancer and cancer conferred by a negative human papillomavirus test. *Journal of the National Cancer Institute* 106, (August, 2014).
12. H. A. Katki et al., Five-year risk of recurrence after treatment of CIN 2, CIN 3, or AIS: performance of HPV and Pap cotesting in posttreatment management. *Journal of lower genital tract disease* 17, S78 (April, 2013).
13. M. Schiffman, N. Wentzensen, Human papillomavirus infection and the multistage carcinogenesis of cervical cancer. *Cancer epidemiology, biomarkers & prevention: a publication of the American Association for Cancer Research, cosponsored by the American Society of Preventive Oncology* 22, 553 (April, 2013).
14. A. F. Fernandez et al., The dynamic DNA methylomes of double-stranded DNA viruses associated with human cancer. Genome research 19, 438 (March, 2009).
15. L. Mirabello et al., Elevated methylation of HPV16 DNA is associated with the development of high grade cervical intraepithelial neoplasia. *International journal of cancer. Journal international du cancer* 132, 1412 (Mar. 15, 2013).
16. N. Wentzensen et al., Methylation of HPV18, HPV31, and HPV45 genomes and cervical intraepithelial neoplasia grade 3. *Journal of the National Cancer Institute* 104, 1738 (Nov. 21, 2012).
17. L. Mirabello et al., Methylation of human papillomavirus type 16 genome and risk of cervical precancer in a Costa Rican population. *Journal of the National Cancer Institute* 104, 556 (Apr. 4, 2012).
18. C. Sun, L. L. Reimers, R. D. Burk, Methylation of HPV16 genome CpG sites is associated with cervix precancer and cancer. *Gynecologic oncology* 121, 59 (April, 2011).
19. N. Vasiljevic, D. Scibior-Bentkowska, A. Brentnall, J. Cuzick, A. Lorincz, A comparison of methylation levels in HPV18, HPV31 and HPV33 genomes reveals similar associations with cervical precancers. *Journal of clinical virology: the official publication of the Pan American Society for Clinical Virology* 59, 161 (March, 2014).
20. N. Vasiljevic, D. Scibior-Bentkowska, A. R. Brentnall, J. Cuzick, A. T. Lorincz, Credentialing of DNA methylation assays for human genes as diagnostic biomarkers of cervical intraepithelial neoplasia in high-risk HPV positive women. *Gynecologic oncology* 132, 709 (March, 2014).
21. A. Lendvai et al., Genome-wide methylation profiling identifies hypermethylated biomarkers in high-grade cervical intraepithelial neoplasia. *Epigenetics: official journal of the DNA Methylation Society* 7, 1268 (November, 2012).
22. J. J. Eijsink et al., A four-gene methylation marker panel as triage test in high-risk human papillomavirus positive patients. *International journal of cancer. Journal international du cancer* 130, 1861 (Apr. 15, 2012).
23. P. Brebi et al., Genome-wide methylation profiling reveals Zinc finger protein 516 (ZNF516) and FK-506-binding protein 6 (FKBP6) promoters frequently methylated in cervical neoplasia, associated with HPV status and ethnicity in a Chilean population. *Epigenetics: official journal of the DNA Methylation Society* 9, 308 (Feb. 1, 2014).
24. A. R. Brentnall et al., A DNA methylation classifier of cervical precancer based on human papillomavirus and human genes. *International journal of cancer. Journal international du cancer* 135, 1425 (Sep. 15, 2014).
25. K. Mendez et al., Urine-based human papillomavirus DNA testing as a screening tool for cervical cancer in high-risk women. *International journal of gynaecology and obstetrics: the official organ of the International Federation of Gynaecology and Obstetrics* 124, 151 (February, 2014).
26. V. V. Sahasrabuddhe et al., Comparison of human papillomavirus detections in urine, vulvar, and cervical samples from women attending a colposcopy clinic. *Journal of clinical microbiology* 52, 187 (January, 2014).
27. C. Payan et al., Human papillomavirus quantification in urine and cervical samples by using the Mx4000 and LightCycler general real-time PCR systems. *Journal of clinical microbiology* 45, 897 (March, 2007).
28. A. Vorsters et al., Optimization of HPV DNA detection in urine by improving collection, storage, and extraction. *European journal of clinical microbiology & infectious diseases: official publication of the European Society of Clinical Microbiology*, (Jun. 12, 2014).
29. A. Vorsters et al., Detection of human papillomavirus DNA in urine. A review of the literature. *European journal of clinical microbiology & infectious diseases: official publication of the European Society of Clinical Microbiology* 31, 627 (May, 2012).
30. A. Ducancelle et al., Interest of Human Papillomavirus DNA quantification and genotyping in paired cervical and urine samples to detect cervical lesions. *Archives of gynecology and obstetrics*, (Mar. 13, 2014).
31. A. V. Lichtenstein, H. S. Melkonyan, L. D. Tomei, S. R. Umansky, Circulating nucleic acids and apoptosis. *Annals of the New York Academy of Sciences* 945, 239 (September, 2001).
32. Y. H. Su et al., Transrenal DNA as a diagnostic tool: important technical notes. *Annals of the New York Academy of Sciences* 1022, 81 (June, 2004).
33. E. M. Shekhtman et al., Optimization of transrenal DNA analysis: detection of fetal DNA in maternal urine. *Clinical chemistry* 55, 723 (April, 2009).
34. H. S. Melkonyan et al., Transrenal nucleic acids: from proof of principle to clinical tests. *Annals of the New York Academy of Sciences* 1137, 73 (August, 2008).
35. A. Cannas et al., *Mycobacterium tuberculosis* DNA detection in soluble fraction of urine from pulmonary tuberculosis patients. *The international journal of tuber-*

36. V. V. Sahasrabuddhe et al., Evaluation of clinical performance of a novel urine-based HPV detection assay among women attending a colposcopy clinic. *Journal of clinical virology: the official publication of the Pan American Society for Clinical Virology*, (May 2, 2014).
37. M. Steinau et al., Performance of commercial reverse line blot assays for human papillomavirus genotyping. *Journal of clinical microbiology* 50, 1539 (May, 2012).
38. I. S. Park et al., Characterization of the methylation patterns in human papillomavirus type 16 viral DNA in head and neck cancers. *Cancer prevention research* 4, 207 (February, 2011).
39. B. Langmead, S. L. Salzberg, Fast gapped-read alignment with Bowtie 2. *Nature methods* 9, 357 (April, 2012).
40. S. F. Altschul et al., Gapped BLAST and PSI-BLAST: a new generation of protein database search programs. *Nucleic acids research* 25, 3389 (Sep. 1, 1997).
41. P. M. Thompson et al., The ENIGMA Consortium: large-scale collaborative analyses of neuroimaging and genetic data. *Brain imaging and behavior* 8, 153 (June, 2014).
42. S. Beaudenon, J. M. Huibregtse, HPV E6, E6AP and cervical cancer. *BMC Biochem* 9 Suppl 1, S4 (2008).
43. D. Dehn, K. C. Torkko, K. R. Shroyer, Human papillomavirus testing and molecular markers of cervical dysplasia and carcinoma. *Cancer* 111, 1 (Feb. 25, 2007).
44. S. K. Kjaer et al., Type specific persistence of high risk human papillomavirus (HPV) as indicator of high grade cervical squamous intraepithelial lesions in young women: population based prospective follow up study. *BMJ* 325, 572 (Sep. 14, 2002).
45. J. Monsonego et al., Cervical cancer control, priorities and new directions. *Int J Cancer* 108, 329 (Jan. 20, 2004).
46. K. S. Cuschieri, M. J. Whitley, H. A. Cubie, Human papillomavirus type specific DNA and RNA persistence—implications for cervical disease progression and monitoring. *J Med Virol* 73, 65 (May, 2004).
47. A. J. Brown, C. L. Trimble, New technologies for cervical cancer screening. *Best practice & research. Clinical obstetrics & gynaecology* 26, 233 (April, 2012).
48. K. Van Doorslaer et al., The Papillomavirus Episteme: a central resource for papillomavirus sequence data and analysis. *Nucleic acids research* 41, D571 (January, 2013).
49. B. Walenz, L. Florea, Sim4db and Leaff: utilities for fast batch spliced alignment and sequence indexing. *Bioinformatics* 27, 1869 (Jul. 1, 2011).
50. F. Krueger, S. R. Andrews, Bismark: a flexible aligner and methylation caller for Bisulfite-Seq applications. *Bioinformatics* 27, 1571 (Jun. 1, 2011).

That which is claimed:

1. A method for triaging a human papillomavirus (HPV)-positive woman into colposcopy, the method comprising:
   (a) selecting a HPV-positive woman testing positive for one or more high risk types of HPV;
   (b) obtaining nucleic acid from a test sample from a liquid prep, plasma, serum or urine of the selected HPV-positive woman;
   (c) performing bisulfite modification to the nucleic acid from the test sample to produce a bisulfite modified nucleic acid;
   (d) determining in the bisulfite modified nucleic acid from (c) a promoter methylation level of the promoter regions of the group of genes comprising ZNF516, FKBP6, and INTS1 and HPV gene HPV16-L1 using quantitative real-time methylation specific PCR (QMSP) and primers and/or probes are selected from the group consisting of SEQ ID NOS: 1-12 that exhibit increased promoter methylation in women having CIN12+ lesions as compared to women having no intraepithelial lesions or malignancy (NILM);
   (e) triaging the HPV-positive woman into colposcopy when the level of promoter methylation of the group of genes is increased relative to the level of promoter methylation of the group of genes in a reference sample obtained from women having NILM; and
   (f) performing a colposcopy.

2. The method of claim 1, wherein selecting the HPV-positive woman testing positive for one or more high risk types of HPV comprises determining whether the nucleic acid is homologous to one or more high risk types of HPV.

3. The method of claim 2, wherein determining whether the nucleic acid is homologous to one or more high risk types of HPV comprises performing at least one HPV detection assay selected from the group consisting of nucleic acid sequencing, PCR, a HPV genotyping assay, a microarray assay, and a mRNA based assay.

4. The method of claim 3, wherein determining whether the nucleic acid is homologous to one or more high risk types of HPV comprises:
   (a) sequencing the nucleic acid to produce a nucleotide sequence;
   (b) performing a sequence alignment between the nucleotide sequence and the nucleotide sequence of the one or more high risk types of HPV; and
   (c) determining the percentage sequence identity between the nucleotide sequence and the nucleotide sequence of the one or more high risk types of HPV.

5. The method of claim 4, wherein the one or more high risk types of HPV are selected from the group consisting of HPV16, HPV18, HPV31, HPV33, HPV35, HPV39, HPV45, HPV51, HPV52, HPV56, HPV58, HPV59, and HPV68.

6. The method of claim 1, wherein the nucleic acid comprises DNA.

7. The method of claim 1, wherein the nucleic acid comprises TrDNA.

8. The method of claim 1, wherein the nucleic acid is from about 150 to about 250 base pairs.

9. The method of claim 1, wherein the HPV-positive woman is further selected on the basis of abnormal cytology.

10. The method of claim 9, wherein the HPV-positive woman has had a negative, positive, or inconclusive Pap smear.

11. The method of claim 1, wherein the method has a specificity of at least 60%.

12. The method of claim 1, wherein the method has a sensitivity of at least 90%.

13. The method of claim 1, wherein the method has a positive predictive value (PPV) of at least 52%.

14. The method of claim 1, wherein the method has a negative predictive value (NPV) of at least 90%.

15. The method of claim 1, further comprising enriching the nucleic acid from the test sample before determining the promoter methylation level; wherein enriching the nucleic acid from the test sample comprises:
   (1) preparing a library of the nucleic acid from the test sample;
   (2) amplifying the library using PCR to form a pre-capture PCR library;
   (3) hybridizing the pre-capture PCR library to a custom-designed pool of HPV-specific and human-specific capture probes to form a post-capture PCR library;
   (4) amplifying the post-capture PCR library to produce enriched nucleic acid; and
   (5) optionally repeating steps (3) and (4).

16. The method of claim 1, further comprising recommending treatment and/or treating the woman, wherein the treatment is selected from the group consisting of removal of precancerous lesions, radiation treatment, surgery, and chemotherapy.

* * * * *